(12) United States Patent
Georgiou et al.

(10) Patent No.: US 8,440,184 B2
(45) Date of Patent: May 14, 2013

(54) COMPOSITIONS OF ENGINEERED HUMAN ARGINASES AND METHODS FOR TREATING CANCER

(75) Inventors: George Georgiou, Austin, TX (US); Everett Stone, Austin, TX (US)

(73) Assignee: GMA Technologies LLC, Austin, TX (US)

( * ) Notice: Subject to any disclaimer, the term of this patent is extended or adjusted under 35 U.S.C. 154(b) by 312 days.

(21) Appl. No.: 12/610,685

(22) Filed: Nov. 2, 2009

(65) Prior Publication Data

US 2010/0111925 A1    May 6, 2010

Related U.S. Application Data

(60) Provisional application No. 61/110,218, filed on Oct. 31, 2008.

(51) Int. Cl.
| | |
|---|---|
| *A61K 38/46* | (2006.01) |
| *C12N 9/14* | (2006.01) |
| *C12N 9/78* | (2006.01) |
| *C12N 9/96* | (2006.01) |
| *C07H 21/04* | (2006.01) |

(52) U.S. Cl.
USPC .......... 424/94.6; 435/195; 435/188; 435/227; 536/23.2

(58) Field of Classification Search .................. None
See application file for complete search history.

(56) References Cited

U.S. PATENT DOCUMENTS

2002/0119554 A1    8/2002   Vockley et al. ............... 435/226

FOREIGN PATENT DOCUMENTS

| EP | 1 803 465 | 7/2007 |
|---|---|---|
| WO | WO 03/063780 | 8/2003 |
| WO | WO 2004/001048 | 12/2003 |

OTHER PUBLICATIONS

Vockley et al. Loss of functional mutations in conserved regions of the human arginase I gene, Biochemical and Molecular Medicine (1996), 59: 44-51.*
Spector et al. Am J Hum Genet (1980), 32: 79-87.*
Ash, "Structure and function of Arginases," *the Journal of Nutrition*, 134:2760S-2764S, 2004.
International Search Report and Written Opinion, issued in Application No. PCT/US2009/062969, mailed Jun. 17, 2010.
Carvajal et al., "Interaction of arginase with metal ions: studies of the enzyme from human liver and comparison with other arginases," *Comp Biochem Physiol B Biochem Mol Biol*, 112:153-159, 1995.
Colleluori et al., "Expression, purification, and characterization of human type II arginase," *Arch Biochem Biophys*, 389:135-143, 2001.
Han et al., "Synthesis and evaluation of alternative substrates for arginase," *Bioorg Chem*, 30:81-94, 2002.
Carvajal et al., "Consequences of mutations of metal ligands in human liver arginase I," *Molecular Biology of the Cell*, 13:546A, 2002.
Rehner et al., "Effect of manganese cobalt and nickel on the activity of liver arginase in-vitro and in-vivo," *Medizin and Ernaehrung*, 11(2):32-35, 1970.
Stone et al., "Engineering human arginase I as a novel cancer therapeutic agent," retrieved from the Internet at http://aiche.conefx.com/aiche/09icbe/preliminaryprogram/abstract_143378.htm, retrieved on Feb. 29, 2012, dated Sep. 6, 2008.
Supplementary European Search Report and Search Opinion issued in European Application No. 09824219.1, mailed May 31, 2012.
Ankudinov et al., "Real-space multiple-scattering calculation and interpretation of x-ray-absorption near-edge structure," *Physical Review B*, 58:7565-7576, 1998.
Aoki et al., "Guanidine is a Zn(2+)-binding ligand at neutral pH in aqueous solution," *J. Am. Chem. Soc.*, 124:5256-5257, 2002.
Ascierto et al., "Pegylated arginine deiminase treatment of patients with metastatic melanoma: results from phase I and II studies," *J. Clin. Oncol.*, 23:7660-7668, 2005.
Auld and Vallee, "Kinetics of carboxypeptidase A. The pH dependence of tripeptide hydrolysis catalyzed by zinc, cobalt, and manganese enzymes," *Biochemistry*, 9:4352-4359, 1970.
Badarau and Page, "The variation of catalytic efficiency of *Bacillus cereus* metallo-betalactamase with different active site metal ions," *Biochemistry*, 45:10654-10666, 2006.
Bansal and Ochoa, "Arginine availability, arginase, and the immune response," *Curr. Opin. Clin. Nutr. Metab. Care.*, 6:223-8, 2003.
Beale and Croft, "A sensitive method for the colorimetric determination of urea," *J. Clin. Pathol.*, 14:418-24, 1961.
Bewley et al., "Crystal structures of *Bacillus caldovelox* arginase in complex with substrate and inhibitors reveal new insights into activation, inhibition and catalysis in the arginase superfamily," *Structure*, 7:435-448, 1999.
Bickmore et al., "Bond-valence methods for pKa prediction. II. Bond-valence, electrostatic, molecular geometry, and solvation effects," *Geochimica et Cosmochimica Acta*, 70:4057-4071, 2006.
Cama et al., "Structural and functional importance of first-shell metal ligands in the binuclear manganese cluster of arginase I," *Biochemistry*, 42:7748-7758, 2003.
Cavalli et al., "Mutagenesis of rat liver arginase expressed in *Escherichia coli*: role of conserved histidines," *Biochemistry*, 33:10652-10657, 1994.
Chaberek et al., "Stability of metal chelates. II. B-hydroxyethyliminodiacetic acid," *J. Am. Chem. Soc.*, 74:5057-60, 1952.
Cheng et al., "Enhanced hepatocyte growth factor signaling by type II transforming growth factor-beta receptor knockout fibroblasts promotes mammary tumorigenesis," *Cancer Res.*, 67:4869-4877, 2007.
Cheng et al., "Pegylated recombinant human arginase (rhArg-peg5,000mw) inhibits the in vitro and in vivo proliferation of human hepatocellular carcinoma through arginine depletion," *Cancer Res.*, 67:309-17, 2007.

(Continued)

*Primary Examiner* — Anand Desai
*Assistant Examiner* — Iqbal H Chowdhury
(74) *Attorney, Agent, or Firm* — Parker Highlander PLLC

(57) ABSTRACT

Compositions and methods for the treatment of cancer are described, and, more preferably, to the treatment of cancers that do not express, or are otherwise deficient in, argininosuccinate synthetase, with enzymes that deplete L-Arginine in serum. In one embodiment, the present invention contemplates an arginase protein, such as a human Arginase I protein, comprising at least one amino acid substitution and a metal cofactor, said protein comprising an increased catalytic activity when compared with a native human Arginase I.

5 Claims, 10 Drawing Sheets

OTHER PUBLICATIONS

Cheng et al., "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma," *Cancer Lett.*, 224:67-80, 2005.

Christianson and Cox, "Catalysis by metal-activated hydroxide in zinc and manganese metalloenzymes," *Annu. Rev. Biochem.*, 68:33-57, 1999.

Christianson and Fierke, "Carbonic anhydrase: evolution of the zinc binding site by nature and by design," *Acc. Chem. Res.*, 29:331-339, 1996.

Di Costanzo et al., "Stereochemistry of guanidine-metal interactions: implications for L-arginine-metal interactions in protein structure and function," *Structure, Function, and Bioinformatics*, 65:637-42, 2006.

Dillion et al., "Biochemical characterization of the arginine degrading enzymes arginase and arginine deiminase and their effect on nitric oxide production," *Med. Sci. Monit.*, 8:BR248-253, 2002.

Dowling et al., "Evolution of the arginase fold and functional diversity," *Cell. Mol. Life Sci.*, 65:2039-55, 2008.

Durante et al., "Arginase: a critical regulator of nitric oxide synthesis and vascular function," *Clin. Exp. Pharmacol. Physiol.*, 34:906-911, 2007.

Ensor et al., "Pegylated arginine deiminase (ADI-SS PEG20,000 mw) inhibits human melanomas and hepatocellular carcinomas in vitro and in vivo," *Cancer Res.*, 62:5443-5450, 2002.

Feun et al., "Clinical trial of CPT-11 and VM-26/VP-16 for patients with recurrent malignant brain tumors," *J. Neurooncol.*, 82:177-181, 2007.

Gill and von Hippel, "Calculation of protein extinction coefficients from amino acid sequence data," *Anal. Biochem.*, 182:319-26, 1989.

He et al., "Aminoguanidinium hydrolysis effected by a hydroxo-bridged dicobalt (II) complex as a functional model for arginase and catalyzed by mononuclear cobalt (II) complexes," *J. Am. Chem. Soc.*, 120:105-113, 1998.

Irving and Williams, "Order of stability of metal complexes," *Nature*, 162:746-747, 1948.

Izzo et al., "Pegylated arginine deiminase treatment of patients with unresectable hepatocellular carcinoma: results from phase I/II studies," *J Clin. Oncol.*, 22:1815-1822, 2004.

Jefferis, "Antibody therapeutics: isotype and glycoform selection," *Expert. Opin. Biol. Ther.*, 7:1401-13, 2007.

Khangulov et al., "L-arginine binding to liver arginase requires proton transfer to gateway residue His141 and coordination of the guanidinium group to the dimanganese(II,II) center," *Biochemistry*, 37:8539-8550, 1998.

Knipp and Vasák, "A colorimetric 96-well microtiter plate assay for the determination of enzymatically formed citrulline," *Anal. Biochem.*, 286:257-64, 2000.

Kuhn et al., "pH-sensitive control of arginase by Mn(II) ions at submicromolar concentrations," *Arch. Biochem. Biophys.*, 286:217-21, 1991.

Lavulo et al., "Subunit-subunit interactions in trimeric arginase. Generation of active monomers by mutation of a single amino acid," *J. Biol. Chem.*, 276:14242-48, 2001.

Lopez et al., "Insights into the interaction of human arginase II with substrate and manganese ions by site-directed mutagenesis and kinetic studies. Alteration of substrate specificity by replacement of Asn149 with Asp," *FEBS J.*, 272:4540-4548, 2005.

McGee et al., "Purification and characterization of *Helicobacter pylori* arginase, RocF: unique features among the arginase superfamily," *Eur. J. Biochem.*, 271:1952-62, 2004.

Mora et al., "Implications of the S-shaped domain in the quaternary structure of human arginase," *Biochemica. Biophysica. Acta.*, 1476:181-90, 2000.

Newville, "IFEFFIT: interactive XAFS analysis and FEFF fitting," *Journal of Synchrotron Radiation*, 8(Pt. 2):322-4, 2001.

Ni et al., "Arginine deiminase, a potential anti-tumor drug," *Cancer Lett.*, 261:1-11, 2008.

Periyannan et al., "Sequential binding of cobalt(II) to metallo-beta-lactamase CcrA," *Biochemistry*, 45:1313-1320, 2006.

Perrin, "421. The hydrolysis of manganese (II) ion," *Journal of the Chemical Society*, pp. 2197-2200, 1962.

Ratilla et al., "Terminal and new bridging coordination of methylguanidine, arginine, and canavanine to platinum (II). The first crystallographic study of bonding between a transition metal and a guanidine ligand, " *Inorganic Chemistry*, 29:918-926, 1990.

Reczkowski and Ash, "Rat liver arginase: kinetic mechanism, alternate substrates, and inhibitors," *Arch. Biochem. Biophys.*, 312:31-7, 1994.

Roopenian and Akilesh, "FcRn: the neonatal Fc receptor comes of age," *Nat. Rev. Immunol.*, 7:715-725, 2007.

Sabio et al., "Glu-256 is a main structural determinant for oligomerisation of human arginase I," *FEBS Lett.*, 501:161-165, 2001.

Santhanam et al., "Inducible NO synthase dependent S-nitrosylation and activation of arginase-1 contribute to age-related endothelial dysfunction," *Circ. Res.*, 101:692-702, 2007.

Sarkissian and Gámez, "Phenylalanine ammonia lyase, enzyme substitution therapy for phenylketonuria, where are we now?" *Mol. Genet. Methab.*, 86(Suppl. 1):S22-6, 2005.

Savoca et al., "Cancer therapy with chemically modified enzymes. II. The therapeutic effectiveness of arginase, and arginase modified by the covalent attachment of polyethylene glycol, on the taper liver tumor and the L5178Y murine leukemia," *Cancer Biochem. Biophys.*, 7:261-268, 1984.

Scolnick et al., "Altering the binuclear manganese cluster of arginase diminishes thermostability and catalytic function," *Biochemistry*, 36:10558-10565, 1997.

Scott et al., "Single amino acid (arginine) deprivation: rapid and selective death of cultured transformed and malignant cells," *Br. J. Cancer*, 83:800-10, 2000.

Segel, Enzyme Kinetics: behavior and analysis of rapid equilibrium and steady state enzyme systems, New York, John Wiley and Sons, Inc., pp. 914-917, 1975.

Shen et al., "Modulation of arginine metabolic pathways as the potential anti-tumor mechanism of recombinant arginine deiminase," *Cancer Lett.*, 231:30-35, 2006.

Simmons et al., "Expression of full-length immunoglobulins in *Escherichia coli*: rapid and efficient production of aglycosylated antibodies," *J. Immunol. Methods*, 263:133-147, 2002.

Stemmler et al., "EXAFS comparison of the dimanganese core structures of manganese catalase, arginase, and manganese-substituted ribonucleotide reductase and hemerythrin," *Biochemistry*, 36:9847-9858, 1997.

Tao and Morrison, "Studies of aglycosylated chimeric mouse-human IgG. Role of carbohydrate in the structure and effector functions mediated by the human IgG constant region," *J. Immunol.*, 143:2595-2601, 1989.

Webb, "SIXPACK: a graphical user interface for XAS analysis using IFEFFIT," *Physica Scripta*, 115:1011-1014.

Wheatley and Campbell, "Arginine catabolism, liver extracts and cancer," *Pathol. Oncol. Res.*, 8:18-25, 2002.

Wheatley, "Arginine deprivation and metabolomics: important aspects of intermediary metabolism in relation to the differential sensitivity of normal and tumour cells," *Semin. Cancer Biol.*, 15:247-253, 2005.

Yoon et al., "Renal cell carcinoma does not express argininosuccinate synthetase and is highly sensitive to arginine deprivation via arginine deiminase," *Int. J. Cancer*, 120:897-905, 2007.

\* cited by examiner

Arginase I Synthetic Sequence
GATATACCATGGGTTCTTCTCACCATCATCACCACCACAGCTCTGGCGAGAACCTGTACTTCCAGTCTGC
GAAGAGCCGTACGATCGGCATTATTGGTGCGCCGTTCTCTAAAGGTCAGCCACGCGGTGGTGTGGAAGAG
GGTCCGACGGTTCTGCGTAAGGCCGGTTTATTAGAAAAGCTGAAAGAGCAGGAGTGCGACGTTAAGGACT
ACGGTGACTTACCATTCGCGGACATCCCGAATGATAGCCCGTTCCAAATCGTTAAGAATCCGCGCTCTGT
GGGTAAAGCAAGCGAGCAGTTAGCAGGTAAGGTGGCCGAGGTCAAGAAAAACGGTCGTATTAGCCTGGTT
TTAGGCGGTGATCATAGCTTAGCAATTGGCTCTATCTCTGGTCATGCCCGTGTGCACCCAGATTTAGGTG
TCATTTGGGTTGACGCCCATACGGATATCAATACGCCATTAACGACCACCAGCGGCAATCTGCATGGCCA
GCCGGTTAGCTTCTTACTGAAGGAGCTGAAGGGTAAAATTCCAGATGTTCCGGGCTTTAGCTGGGTCACG
CCATGTATTTCTGCCAAGGATATCGTGTACATTGGCTTACGTGACGTCGACCCAGGTGAGCACTACATCT
TAAAGACCCTGGGTATCAAGTATTTCAGCATGACGGAAGTGGACCGCTTAGGCATCGGCAAGGTGATGGA
GGAGACGCTGAGCTATCTGCTGGGCCGTAAGAAACGTCCAATCCATCTGAGCTTCGATGTTGACGGCTTA
GACCCGAGCTTTACGCCAGCCACCGGCACGCCGGTCGTTGGTGGTTTAACGTATCGCGAAGGCCTGTATA
TCACGGAGGAAATCTATAAGACGGGTTTACTGAGCGGTCTGGACATTATGGAGGTTAATCCAAGCTTAGG
TAAGACGCCGGAAGAAGTTACCCGTACCGTTAACACGGCGGTCGCGATCACGTTAGCATGTTTCGGTTTA
GCCCGCGAGGGCAACCATAAACCAATTGATTATCTGAATCCACCGAAGTGAGGATCCGAATTCG Arginase II Synthetic Sequence
GATATACCATGGGCAGCAGCCATCATCACCACCATCACAGCTCTGGTGAAAACTTATACTTCCAAAGCGT
CCATAGCGTCGCAGTGATTGGTGCCCCGTTTAGCCAAGGTCAAAAACGCAAGGGTGTTGAACATGGTCCG
GCAGCGATCCGCGAAGCAGGTTTAATGAAGCGTTTAAGCAGCTTAGGCTGTCACTTAAAGGATTTCGGTG
ATTTAAGCTTTACGCCGGTCCCAAAGGATGATTTATACAATAATCTGATCGTTAACCCACGCTCTGTGGG
TCTGGCGAACCAGGAGCTGGCGGAGGTCGTGTCTCGTGCAGTCAGCGACGGTTATAGCTGCGTTACGCTG
GGCGGTGATCATAGCTTAGCCATTGGTACGATTTCTGGTCATGCCCGCCATTGCCCGGATCTGTGTGTTG
TGTGGGTTGATGCGCACGCGGATATCAATACGCCACTGACCACGTCTAGCGGTAATTTACACGGCCAGCC
GGTTAGCTTCTTATTACGTGAGCTGCAAGACAAGGTCCCGCAGTTACCAGGCTTCTCTTGGATCAAACCA
TGTATCAGCAGCGCATCTATTGTCTACATTGGCCTGCGTGATGTCGACCCACCGGAGCACTTCATCCTGA
AGAATTATGACATCCAGTATTTCAGCATGCGTGACATCGACCGTCTGGGTATCCAAAAAGTTATGGAGCG
CACGTTCGATCTGTTAATCGGCAAGCGCCAGCGTCCGATTCACCTGAGCTTTGACATTGACGCCTTTGAC
CCGACCCTGGCCCCAGCAACGGGCACGCCAGTGGTTGGTGGTTTAACCTACCGTGAGGGTATGTATATTG
CAGAAGAGATCCATAATACCGGCCTGTTATCTGCCCTGGATCTGGTTGAAGTCAATCCGCAGCTGGCAAC
CTCTGAGGAGGAAGCGAAGACGACCGCCAACCTGGCGGTGGACGTCATCGCCTCTTCTTTCGGCCAGACG
CGTGAAGGTGGCCATATCGTGTATGACCAATTACCAACGCCATCTAGCCCGGACGAATCTGAGAACCAAG
CACGTGTCCGTATTTGAGGATCCGAATTCG

FIG. 1

8 % Native Gel, 90 V, pH 9.5
Tris-Gly, 3 hr, 4 C.

COMPOSITIONS OF ENGINEERED HUMAN ARGINASES AND METHODS FOR TREATING CANCER

CROSS-REFERENCE TO RELATED APPLICATIONS

This applications claims the priority of U.S. Provisional Patent Application Ser. No. 61/110,218, filed Oct. 31, 2008, the entire disclosure of which is specifically incorporated herein by reference.

STATEMENT REGARDING FEDERALLY SPONSORED RESEARCH OR DEVELOPMENT

This invention was made with government support under R01 CA139059 awarded by the National Institutes of Health. The government has certain rights in the invention.

BACKGROUND OF THE INVENTION

1. Field of the Invention

The invention generally relates to compositions and methods for the treatment of cancer with enzymes that deplete L-Arginine in serum. In some embodiments, the cancer is one that does not express, or is otherwise deficient in, argininosuccinate synthetase (ASS), ornithine transcarbamylase (OTC), or other enzymes required for arginine biosynthesis.

2. Description of the Related Art

It has been recognized for over 50 years that certain tumor cells have a high demand for amino acids, such as L-Arginine and are killed under conditions of L-Arginine depletion (Wheatley and Campbell, 2002). In human cells L-Arginine is synthesized in two steps; first argininosuccinate synthetase (ASS) converts L-Citrulline and aspartate to argininosuccinate, followed by conversion of argininosuccinate to L-Arginine and fumarate by argininosuccinate lyase. L-Citrulline itself is synthesized from L-Ornithine and carbamoyl phosphate by the enzyme ornithine transcarbamylase (OTC). A large number of hepatocellular carcinomas, melanomas and, as discovered recently, renal cell carcinomas (Ensor et al., 2002; Feun et al., 2007; Yoon et al., 2007) do not express ASS and thus are sensitive to L-Arginine depletion. The molecular basis for the lack of ASS expression appears to be diverse and includes aberrant gene regulation and splicing defects. Whereas non-malignant cells enter into quiescence ($G_0$) when depleted of L-Arginine and thus remain viable for several weeks, tumor cells have cell cycle defects that lead to the re-initiation of DNA synthesis even though protein synthesis is inhibited, in turn resulting in major imbalances and rapid cell death (Shen et al., 2006; Scott et al., 2000). The selective toxicity of L-Arginine depletion for HCC, melanoma and other ASS-deficient cancer cells has been extensively demonstrated in vitro, in xenograft animal models and in clinical trials (Ensor et al., 2002; Feun et al., 2007; Shen et al., 2006; Izzo et al., 2004). Recently Cheng et al. (2007) demonstrated that many HCC cells are also deficient in ornithine transcarbamylase expression and thus, they are also susceptible to enzymatic L-Arginine depletion.

There is interest in the use of L-Arginine hydrolytic enzymes for cancer therapy, especially the treatment of hepatocarcinomas, melanomas and renal cell carcinomas, which are common forms of cancer associated with high morbidity. Two L-Arginine degrading enzymes have been used for cancer therapy: bacterial arginine deiminase and human Arginases. Unfortunately, both of these enzymes display significant shortcomings that present major impediments to clinical use (immunogenicity and low catalytic catalytic activity and very poor stability in serum, respectively). Thus, the therapeutic success of L-Arginine depletion therapy will rely on addressing these shortcomings.

SUMMARY OF THE INVENTION

The invention generally relates to compositions and methods for the treatment of cancer with enzymes that deplete L-Arginine in serum. In some embodiments, the cancer is one that does not express, or is otherwise deficient in, argininosuccinate synthetase (ASS), ornithine transcarbamylase (OTC), or other enzymes required for arginine biosynthesis.

In some aspects, the present invention contemplates arginase proteins wherein the natural metal cofactor ($Mn^{2+}$) is replaced with another metal. In particular embodiments, the arginase protein comprises an amino acid sequence of human Arginase I or an amino acid sequence of human Arginase II and a non-native metal cofactor. In some embodiments, the metal is cobalt ($Co^{2+}$). Human Arginase I and II proteins of the present invention have two Mn (II) sites; either or both sites can be substituted so as to generate a mutatated Arginase I or II protein with a non-native metal cofactor. In some embodiments, the protein displays a $k_{cat}/K_m$ greater than 400 $mM^{-1} s^{-1}$ at pH 7.4. In a particular embodiment, the protein displays a $k_{cat}/K_m$ between 400 $mM^{-1} s^{-1}$ and 4,000 $mM^{-1} s^{-1}$ at pH 7.4. In another embodiment, the protein displays a $k_{cat}/K_M$ between 400 $mM^{-1} s^{-1}$ and 2,500 $mM^{-1} s^{-1}$ at pH 7.4 at 37° C. In a particular embodiment, the present invention contemplates a protein comprising an amino acid sequence of human Arginase I or II and a non-native metal cofactor, wherein said protein exhibits a $k_{cat}/K_m$ greater than 400 $mM^{-1} s^{-1}$ at 37° C., pH 7.4.

In some embodiments, the native arginase is modified only by the substitution of the metal cofactor. In other embodiments, the arginase is modified by substitution of the metal cofactor in addition to other modifications, such as substitutions, deletions, and truncations. In a particular embodiment, the invention provides a protein comprising a native amino acid sequence of human Arginase I or II and a non-native metal cofactor, wherein the amino acid sequence is lacking part of the native sequence. In particular embodiments, the non-native metal cofactor is cobalt. In some embodiments, the amino acid sequence of human Arginase I comprises SEQ ID NO:1. In other embodiments, the amino acid sequence of human Arginase II comprises SEQ ID NO:2. In yet other embodiments, the arginase lacks a portion of the wild-type sequence. In other embodiments, the amino acid sequence comprises a truncated Arginase I or Arginase II sequence. In a particular embodiment, the arginase is Arginase II and lacks the first 21 amino acids of the wild-type sequence. In another embodiment, the native arginases lacks an N-terminal methionine.

In another aspect, the present invention contemplates an arginase protein comprising at least one amino acid substitution, wherein the protein displays an increased catalytic activity under physiological conditions and especially at the pH of human serum (pH 7.4) when compared with native human Arginase I or II protein. In some embodiments, the arginase protein is a human Arginase I protein or human Arginase II protein. In some embodiments, the protein further comprises a non-native metal cofactor. In particular embodiments, the non-native metal cofactor is $Co^{+2}$. Substitution of the $Mn^{+2}$ cofactor with $Co^{+2}$ results in marked increase in catalytic activity and a drastic reduction in $K_m$ at physiological pH.

In one embodiment, the present invention provides a human Arginase I protein comprising at least one amino acid substitution at the metal binding site, wherein the protein displays an increase in the hydrolysis of Arginine that results in a $k_{cat}/K_m$ of at least two fold greater than that of a native human Arginase I having SEQ ID NO:1. In another embodiment, the present invention provides a human Arginase II protein comprising at least one amino acid substitution at the metal binding site, wherein the protein displays an increase in the hydrolysis of Arginine that results in a $k_{cat}/K_m$ of at least two fold greater than that of a native human Arginase II having SEQ ID NO:2. In some embodiments, the protein displays a $k_{cat}/K_m$ greater than 400 mM$^{-1}$ s$^{-1}$ at pH 7.4. In a particular embodiment, the protein displays a $k_{cat}/K_m$ between 400 mM$^{-1}$ s$^{-1}$ and 4,000 mM$^{-1}$ s$^{-1}$ at pH 7.4. In another embodiment, the protein displays a $k_{cat}/K_M$ between 400 mM$^{-1}$ s$^{-1}$ and 2,500 mM$^{-1}$ s$^{-1}$ at pH 7.4 at 37° C. In some aspects, the invention provides mutations that increase the stability of human arginases in serum relative to the stability of native human arginases.

In some embodiments, the amino acid substitution is at His101, Asp124, His126, Asp128, Asp232, Asp234, Trp122, Asp181, Ser230, His120, Asp143, His145, Asp147, Asp251, Asp253, Trp141, Asp200, Ser249, Cys303, or Glu256. A number of mutations have been found to increase the catalytic activity and drastically reduce the $K_m$ for L-Arginine under physiological conditions. In some embodiments, mutations are substitution mutations selected from the group consisting of Asp181Ser, Ser230Cys, Ser230Gly, Cys303Phe, Cys303Ile, Glu256Gln, Asp181Glu and Ser230Ala. In some aspects, the present invention provides embodiments where two or more mutations are introduced in human arginase. In some embodiments, the human arginase protein comprises at least two amino acid substitutions. In a particular embodiment, the substitutions are Asp181Glu and Ser230Ala.

In some aspects, the present invention provides arginases comprising additional changes relative to the wild-type or native protein. In some embodiments, the changes include substitution, deletions (e.g. lacking part of the native sequence), truncations, or a combination thereof. In some embodiments, the present invention also contemplates native arginases, wherein the only amino acid sequence changes are deletions. In a particular embodiment, the present invention contemplates a human Arginase I protein, wherein the protein lacks an N-terminal methionine. Other and larger deletions are also contemplated for the various mutant arginases described herein. For example, truncated Arginase lacking the 14 C-terminal amino acids has been reported, leaving Arg-308 as the last residue in the sequence (Mora et al., 2000). In yet another embodiment, the arginase lacks the first 21 amino acids of the wild-type sequence.

In some aspects, the present invention also contemplates fusion proteins comprising an arginase linked to a non-arginase amino acid sequence. In one embodiment, the non-arginase sequence comprises at least a portion of the Fc region of an immunoglobulin, e.g., to increase the half-life of the arginase in serum when administered to a patient. The Fc region or portion thereof may be any suitable Fc region. In one embodiment, the Fc region or portion thereof is an IgG Fc region. In some embodiments, the amino acid sequence having arginase activity is selected from the group consisting of a native or mutated amino acid sequence of human Arginase I and a native or mutated amino acid sequence of human Arginase II. In one embodiment, a dimeric Fc-Arginase fusion protein is contemplated.

The arginase in the fusion protein may be native, mutated, and/or otherwise modified, e.g., metal cofactor modified. In some embodiments, the arginase may contain deletions, substitutions, truncations or a combination thereof. In a particular embodiment, the present invention contemplates an Fc-arginase containing fusion protein, wherein the arginase is an Arginase I. In one embodiment, the arginase lacks a portion of the wild-type sequence. In another embodiment, the arginase is Arginase I lacking an N-terminal methionine. In yet another embodiment, the arginase is Arginase II, wherein the Arginase II lacks the first 21 amino acids of the wild-type Arginase II sequence. In some embodiments, the arginase further comprise a non-native metal cofactor. In these embodiments, either or both sites can be substituted to generate a fusion protein comprising an amino acid sequence of human Arginase I or II and a non-native metal cofactor. In some embodiments, the non-native metal cofactor is cobalt. In some embodiments, the arginase contains a substitution. In one embodiment, the substitution is Glu256Gln. In another embodiment, the substitution is Asp181Ser. In yet another embodiment, the substitution is Ser230Cys. In still another embodiment, the substitution is Ser230Gly. In yet another embodiment, the substitution is Cys303Phe. In still another embodiment, the substitution is Cys303Ile. In some embodiments, the human Arginase I comprises at least two amino acid substitutions. In one embodiment, the substitutions are Asp181Glu and Ser230Asp.

In some aspects, the present invention further contemplates nucleic acid encoding such arginases. In some embodiments, the nucleic acid that has been codon optimized for expression in bacteria. In particular embodiments, the bacteria is *E. coli*. In other aspects, the present invention further contemplates vectors containing such nucleic acids. In particular embodiments, the nucleic acid encoding the mutant arginase is operably linked to a promoter, including but not limited to heterologous promoters. In still further aspects, the present invention further contemplates host cells comprising such vectors. In some embodiments, the host cells are transfected or transformed host cells expressing the mutant arginases. The proteins may be expressed in any suitable manner. In one embodiment, the proteins are expressed in a host cell such that the protein is glycosylated. In another embodiment, the proteins are expressed in a host cell such that the protein is aglycosylated.

The present invention also contemplates methods of treatment by the administration of the arginase proteins of the present invention, and in particular methods of treating subjects with cancer. In some embodiments, the cancer is one that does not express, or is otherwise deficient in, argininosuccinate synthetase (ASS) or ornithine transcarbamylase (OTC). In particular embodiments, the human cancer is an arginine auxotrophic cancer. As discussed above, the arginase protein may be native, mutated, and/or otherwise modified, e.g., metal cofactor modified. In one embodiment, the present invention contemplates a method of treating a human cancer patient comprising administering a formulation comprising a fusion protein, the fusion protein comprising an amino acid sequence having arginase activity and at least a portion of the Fc region of a human immunoglobulin to the patient. In some embodiments, the administration occurs under conditions such that at least a portion of the cancer cells of the cancer are killed. In another embodiment, the formulation comprises an amino acid sequence having human arginase activity higher than that displayed by the authentic human arginases at physiological conditions and further comprising an attached polyethylene glycol chain. In some embodiment, the formulation is a pharmaceutical formulation comprising any of the above discussed arginase proteins and a pharmaceutically acceptable excipients. Such pharmaceutically acceptable excipients are well known to those having skill in the art. All of the above arginase variants are contemplated as useful for human therapy.

The cancer may be any type of cancer or tumor type. In some embodiments, the cancer is hepatocellular carcinoma, renal cell carcinoma, melanoma, prostate cancer, or pancreatic cancer. In some embodiments, the formulation is administered topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, subcutaneously, subconjunctival, intravesicularlly, mucosally, intrapericardially, intraumbilically, orally, by inhalation, by injection, by infusion, by continuous infusion, by localized perfusion bathing target cells directly, via a catheter, or via a lavage. In one embodiment, to increase serum half-life, the arginase variants described herein are "pegylated."

All of the above mentioned arginases, variants and the like are contemplated in a preferred embodiment as purified or isolated proteins, and preferably monomeric proteins.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The term "therapeutically effective" as used herein refers to an amount of cells and/or therapeutic composition (such as a therapeutic polynucleotide and/or therapeutic polypeptide) that is employed in methods of the present invention to achieve a therapeutic effect, such as wherein at least one symptom of a condition being treated is at least ameliorated, and/or to the analysis of the processes or materials used in conjunction with these cells.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1 shows Arginase I (SEQ ID NO:1) and Arginase II (SEQ ID NO:2) nucleic acid sequences.

FIG. 7A demonstrates the survival of HCC tissue culture (Hep3b) when treated with 0-100 nM Arginase (Day 5). Mn-hArgI (▲), resulted in an apparent IC$_{50}$ of 5±0.3 nM (~0.18 μg/ml). Incubations with Co-hArgI (•) lead to a 15-fold increase in cytotoxicity with an apparent IC$_{50}$ of 0.33±0.02 nM (~0.012 μg/ml). FIG. 7B is a graph showing the effect hArgI on the growth A375 melanoma cells (Day 5). Mn-hArgI (▲), resulted in an apparent IC$_{50}$ of 4.1±0.1 nM (~0.15 μg/ml). Incubation with Co-hArgI (•) lead to a 13-fold increase in cytotoxicity with an apparent IC50 of 0.32±0.06 nM (~0.012 μg/ml).

FIG. 12 14-20% SDS-PAGE showing hArgI conjugated to PEG MW 5000, with an apparent MW of ~150 kDa.

DESCRIPTION OF THE ILLUSTRATIVE EMBODIMENTS

Figure 2:
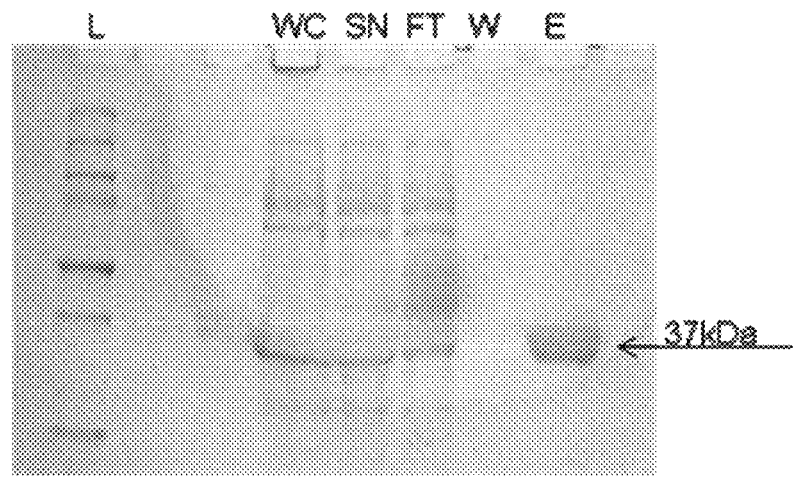
FIG. 2 is a photograph of a SDS-PAGE showing purification steps for human Arginase I. L=Molecular Weight Ladder; WC=Whole Cell Fraction, SN=Supernatant; FT=Flow Through from IMAC Column; W=Column Wash; E=Arginase Elution Fraction.

The invention generally relates to compositions and methods for the treatment of cancer with enzymes that deplete L-Arginine in serum. In some embodiments, the cancer is one that does not express, or is otherwise deficient in, argininosuccinate synthetase (ASS), ornithine transcarbamylase (OTC), or other enzymes required for arginine biosynthesis. Both native and mutated enzymes are contemplated, as well as enzymes with modified metal cofactors, enzymes fused to other polypeptides as well as enzymes conjugated to polymers that increase serum persistence, e.g., high molecular weight polyethylene glycol I. Arginase Arginase is a manganese-containing enzyme. It is the final enzyme of the urea cycle. Arginase is the fifth and final step in the urea cycle, a series of biophysical reactions in mammals during which the body disposes of harmful ammonia. Specifically, arginase converts L-arginine into L-ornithine and urea.

L-Arginine is the nitrogen donating substrate for nitric oxide synthase (NOS), producing L-Citrulline and NO. Although the $K_M$ of Arginase (2-5 mM) has been reported to be much higher than that of NOS for L-Arginine (2-20 µM), Arginase may also play a role in regulating NOS activity. Under certain conditions Arginase I is Cys-S-nitrosylated, resulting in higher affinity for L-Arginine and reduced availability of substrate for NOS.

Arginase is a homo-trimeric enzyme with an α/β fold of a parallel eight-stranded β-sheet surrounded by several helices. The enzyme contains a di-nuclear metal cluster that is integral to generating a hydroxide for nucleophilic attack on the guanidinium carbon of L-Arginine. The native metal for Arginase is $Mn^{2+}$. These $Mn^{2+}$ ions coordinate water, orientating and stabilizing the molecule and allowing water to act as a nucleophile and attack L-arginine, hydrolyzing it into ornithine and urea.

Mammals have two Arginase isozymes (EC 3.5.3.1) that catalyze the hydrolysis of L-Arginine to urea and L-Ornithine. The Arginase I gene is located on chromosome 6 (6q.23), is highly expressed in the cytosol of hepatocytes, and functions in nitrogen removal as the final step of the urea cycle. The Arginase II gene is found on chromosome 14 (14q.24.1). Arginase II is mitochondrially located in tissues such as kidney, brain, and skeletal muscle where it is thought to provide a supply of L-Ornithine for proline and polyamine biosynthesis (Lopez et al., 2005).

Arginases have been investigated for nearly 50 years as a method for degrading extracellular L-Arginine (Dillon et al., 2002). Some promising clinical results have been achieved by introducing Arginase by transhepatic arterial embolisation; following which, several patients experienced partial remission of HCC (Cheng et al., 2005). However, since Arginase has a high $K_M$ (~2-5 mM) and exhibits very low activity at physiological pH values, high dosing is required for chemotherapeutic purposes (Dillon et al., 2002). While native Arginase is cleared from circulation within minutes (Savoca et al., 1984), a single injection of PEG-Arginase MW5000 in rats was sufficient to achieve near complete arginine depletion for ~3 days (Cheng et al., 2007).

Cheng et al. made the surprising observation that many human HCC cells lines do not express OTC (in addition to ASS) and thus they are susceptible to PEG-Arginase (Cheng et al., 2007). In mice implanted with Hep3b hepatocarcinoma cells weekly administration of PEG-Arginase resulted in tumor growth retardation which was accentuated by co-administration of 5-fluorouracil (5-FU). However, PEG-Arginase was used at the very high doses that are impractical for human therapy, reflecting its lower physiological activity.

To address these issues a bacterial arginine hydrolyzing enzyme, Arginine Deiminase or ADI which displays good kinetics and stability has been tested in vitro. A PEGylated form of ADI is now undergoing Phase II/III clinical trials. Unfortunately ADI is a bacterial enzyme and therefore it induces strong immune responses and adverse effects in most patients. However, for those patients that do not develop significant adverse responses, an impressive percentage exhibit stable disease or remission. Nonetheless because of its unfavorable immunological profile it is unlikely that L-Arginine depletion by ADI will become a mainstream treatment for liver cancer.

For clinical use, it is essential that the arginase is engineered to allow it to persist for long times (e.g., days) in circulation. In the absence of any modification, human arginase has a half life of only a few minutes in circulation primarily because its size is not sufficiently large to avoid filtration though the kidneys. Unmodified human Arginase is very susceptible to deactivation in serum and it is degraded with a half life of only four hours. Therefore, the present invention developed novel and improved forms of arginase for clinical research and potential therapeutic use with improved circulation persistence.

II. Arginase Variants

Mammals have two Arginase isozymes (EC 3.5.3.1) that catalyze the hydrolysis of L-Arginine to urea and L-Ornithine. The Arginase I gene is located on chromosome 6 (6q.23), is highly expressed in the cytosol of hepatocytes, and functions in nitrogen removal as the final step of the urea cycle. The Arginase II gene is found on chromosome 14 (14q.24.1). Arginase II is mitochondrially located in tissues such as kidney, brain, and skeletal muscle where it is thought to provide a supply of L-Ornithine for proline and polyamine biosynthesis (Lopez et al., 2005).

Figure 4:
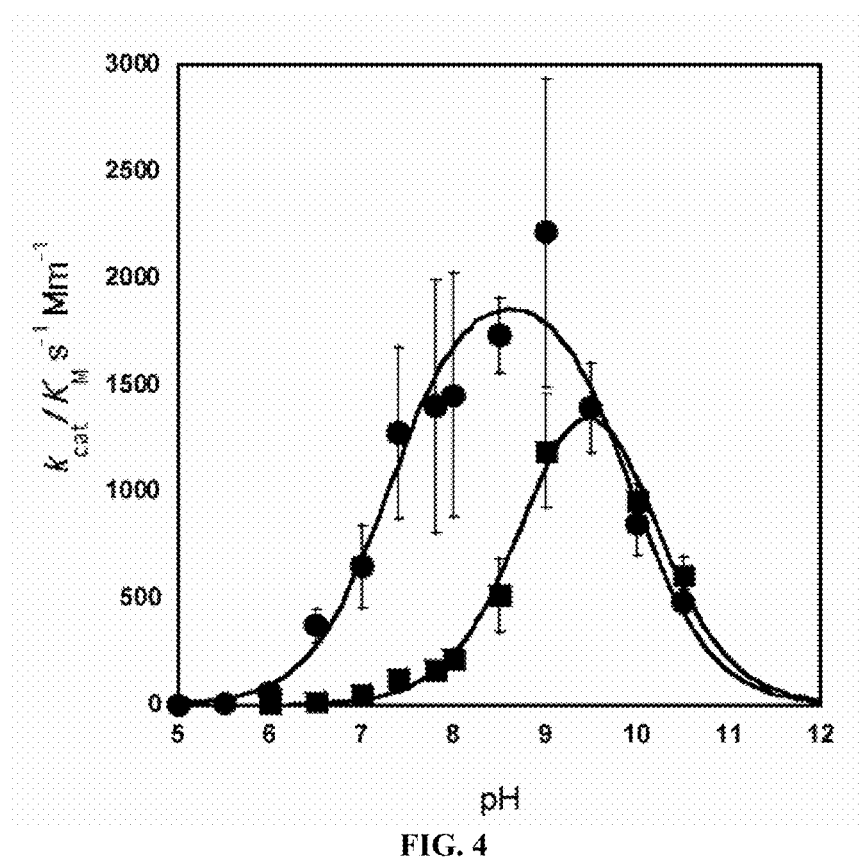
FIG. 4 is a plot of $k_{cat}/K_M$ versus pH for Co-hArgI (•) with an ascending limb p$K_a$ of 7.5 and Mn-hArgI (■) with an ascending limb p$K_a$ of 8.5.
Figure 5:
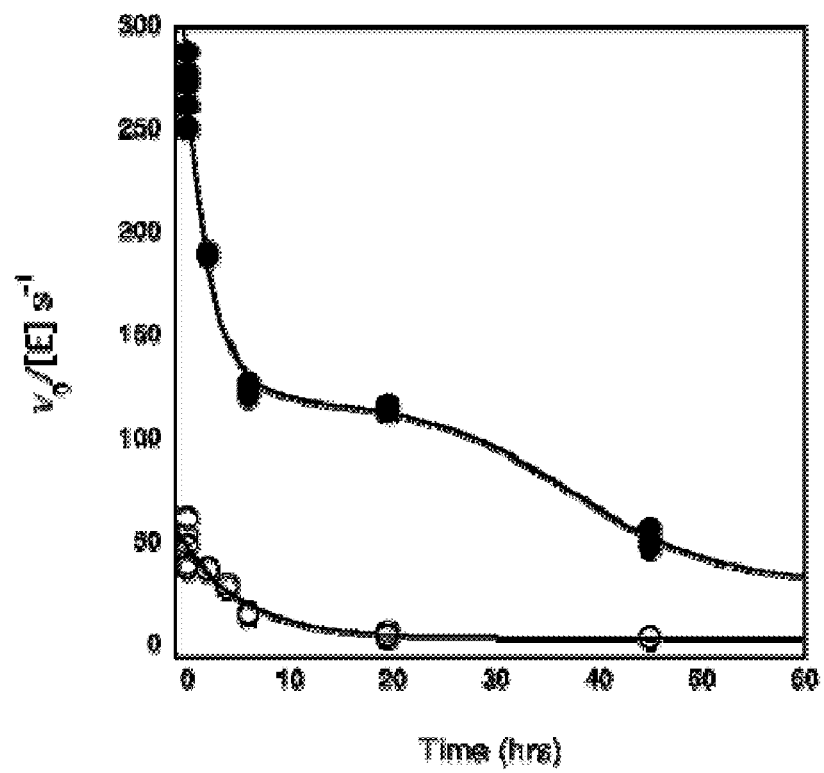
FIG. 5 is a graph showing the stability of Co-hArgI and Mn-hArgI (1 μM) incubated in pooled human serum at 37° C. over time in pooled human serum. Aliquots were withdrawn over time and assayed against 1 mM of L-Arg in a 100 mM Hepes buffer, pH 7.4, at 37° C. Mn-hArgI (○) displayed an exponential loss of activity with a T ½ life of 4.8±0.8 hrs. In contrast Co-hArgI (•) displayed a bi-phasic loss of activity with an apparent first T½ of 6.1±0.6 hrs followed by much longer second T ½ of 37±3 hrs.

L-Arginine is the sole substrate for nitric oxide synthase (NOS), producing L-Citrulline and NO. Although the $K_M$ of Arginase (2-5 mM) has been reported to be much higher than that of NOS for L-Arginine (2-20 µM), Arginase may also play a role in regulating NOS activity (Durante et al., 2007). Under certain conditions Arginase I is Cys-S-nitrosylated, resulting in higher affinity for L-Arginine and reduced availability of substrate for NOS (Santhanam et al., 2007). Arginase is a homo-trimeric enzyme with an α/β fold of a parallel eight-stranded β-sheet surrounded by several helices. The enzyme contains a di-nuclear metal cluster that is integral to generating a hydroxide for nucleophilic attack on the guanidinium carbon of L-Arginine (Cama et al., 2003; Dowling et al., 2008). The native metal for Arginase is $Mn^{2+}$. Arginase with the native metal (i.e. Mn2+) exhibits a pH optimum of 9. At physiological pH the enzyme exhibits more than a 10-fold lower $k_{cat}/K_m$. in the hydrolysis of L Arginine (FIG. 4). The low catalytic activity displayed by the authentic human arginase with the native $Mn^{2+}$ enzyme presents a problem for human therapy since it means that impractical doses of the enzyme have to be used to achieve a therapeutically relevant reduction in L-Arginine plasma levels.

In some aspects, the present invention contemplates mutant arginases wherein the natural metal cofactor ($Mn^{2+}$) is replaced with another metal. It has been found that substitution of the metal cofactor in human arginase exerts a beneficial effect on the rate of hydrolysis of L-Arginine and stability under physiological conditions when compared to native human arginase with the natural metal cofactor. The substitution of the native metal ($Mn^{2+}$) with other divalent cations can be exploited to shift the pH optimum of the enzyme to a lower values and thus achieve high rates of L-arginine hydrolysis under physiological conditions. Human Arginase I and II proteins of the present invention have two Mn (II) sites;

therefore, either or both sites can be substituted so as to generate a mutatated Arginase I or II protein with a non-native metal cofactor.

In some embodiments, the metal is cobalt ($Co^{2+}$). Incorporation of Co2+ in the place of $Mn^{2+}$ in human Arginase I or human Arginase II results in dramatically higher activity at physiological pH. It was found that an enzyme containing $Co^{2+}$ ("Co-hArgI") displayed a 10 fold increase in $k_{cat}/K_M$ in vitro at pH 7.4, which in turn translated into a 15 fold increase in HCC cytotoxicity and a 13-fold increase in melanoma cytotoxity as compared to the human Arginase I which contains $Mn^{2+}$. It was also found that a pharmacological preparation of Co-hArgI could clear serum L-Arg for over 3 days in mice with a single injection. Furthermore, it was found that a pharmacological preparation of Co-hArgI could shrink HCC tumor xenografts in nude mice whereas Mn-hArgI only slowed tumor growth (Ensor et al., 2002).

In some embodiments, the present invention provides a human arginase protein comprising at least one amino acid substitution at the metal binding site. The structure of Arginase shows an active site cleft containing two $Mn^{2+}$ ions, with the more deeply localized ion designated $Mn_A$ coordinated to H101, D124, D128, D232 and bridging hydroxide. The other metal is designated $Mn_B$ and is coordinated by H126, D124, D232, D234 and bridging hydroxide (Christianson and Cox, 1999). The residues comprising the metal binding site for the first shell of Arginase I are H101, D124, H126, D128, D232, and D234 and for the second shell are W122, D181, and S230. Similarly, the residues comprising the metal binding site for the first shell of Arginase II are H120, D143, H145, D147, D251, D253 and for the second shell are W141, D200, S249.

Arginase has been shown to require both $Mn^{2+}$ ions for full activity, however $Mn_A$ can be reversibly dissociated resulting in an enzyme with half its catalytic activity (Scolnick et al., 1997). Metal (A) of hArgI is coordinated to the imidazole of H101, which is in turn hydrogen bonded to the hydroxyl of S230. Metal (B) of hArgI is coordinated to the imidazole of H126, which has a $2^{nd}$ shell hydrogen bond with the carboxyl of D181. The positions involved in the binding of the metal were subjected to saturation mutagenesis and the resulting libraries were screened using a microtiter well plate assay for arginase activity (described in more detail below in the examples) to isolate clones expressing proteins that display higher catalytic activity. Novel clones were identified by sequencing, re-transformed into *E. coli* (BL21) and purified and kinetically characterized as described below in the examples. Variants displaying apparent activity $\gtreqqless$ to wild-type were purified in larger scale and assayed for their steady-state kinetic parameters of $k_{cat}$ & $K_M$. The following variants were found to have greater $k_{cat}/K_M$ constants than Co-hArgI: D181S, D181E/S230A (double mutant containing two substitutions). Similarly the amino acid substitutions S230C and S230G were found to have a particularly important effect on catalytic activity and also on serum stability. Additionally, amino acids removed from the metal binding site were also subjected to combinatorial saturation mutagenesis. For example, it was found that a C303P substitution in Co-hArg I conferred a 10-fold higher $k_{cat}/K_M$ relative to the native Mn-hArg I at pH 7.4. Many of these variant or mutant forms of the arginase are contemplated for use in the treatment of cancer, including where they are made as fusion proteins, e.g. with an Fc region (or portion thereof) of an immunoglobulin (in order to increase half-life).

The $Cys_{303}$ variants were also tested for serum stability. It was found that a C303P variant, i.e. a single amino acid substitution in Arginase, exhibits a ~60% increase in serum stability which in turn translates into a 30 fold increase in HCC cytotoxicity as compared to the Mn substituted enzyme at pH 7.4. In one embodiment, the present invention contemplates treatment with this novel enzyme or this novel enzyme with further mutations. In a particular embodiment, this novel enzyme is employed for treatment as an Arginase-Fc protein fusion that capitalizes on the endosomal recycling of the IgG fc domain to ensure long serum persistence of the Arginase variant. Long serum persistence improves the use of Arginase as a therapeutic.

III. Pegylation

In certain aspects of the invention, methods and compositions related to pegylated arginase are disclosed. Specifically, pegylation of arginase at an engineered Cysteine residue (e.g., substituting the third residue of the N-terminal) may be used to produce a homogenous pegylated arginase composition. Methods for isolation of pegylated arginase based on temporary disruption of polymerization are also disclosed.

Pegylation is the process of covalent attachment of poly (ethylene glycol) polymer chains to another molecule, normally a drug or therapeutic protein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins.

The first step in pegylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation pegylation chemistry more efficient functional groups such as aldehyde, esters, amides etc. made available for conjugation.

As applications of pegylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific pegylation at native cysteinyl residues is seldom carried out, since these residues are usually in the form of disulfide bonds or are required for biological activity. On the other hand, site-directed mutagenesis can be used to incorporate cysteinyl pegylation sites for thiol-specific linkers. The cysteine mutation must be designed such that it is accessible to the pegylation reagent and is still biologically active after pegylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the pegylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However; this chemical is highly toxic and must be handled cautiously, particularly at lower pH where it becomes volatile.

Due to the multiple lysine residues on most proteins, site-specific pegylation can be a challenge. Fortunately, because these reagents react with unprotonated amino groups, it is possible to direct the pegylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However; this is only feasible if the N-terminal portion of the protein is not required for biological activity. Still, the pharmacokinetic benefits from pegylation frequently outweigh a significant loss of in vitro bioactivity, resulting in a product with much greater in vivo bioactivity regardless of pegylation chemistry.

There are several parameters to consider when developing a pegylation procedure. Fortunately, there are usually no more than four or five key parameters. The "design of experiments" approach to optimization of pegylation conditions can be very useful. For thiol-specific pegylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the pegylation reaction. For example, if the pegylation agent is only 70 percent active, the amount of PEG used should ensure that only active PEG molecules are counted in the protein-to-PEG reaction stoichiometry. How to determine PEG reactivity and quality will be described later.

IV. Proteins and Peptides

In certain embodiments, the present invention concerns novel compositions comprising at least one protein or peptide, such as stabilized arginase multimers. These peptides may be comprised in a fusion protein or conjugated to an agent as described supra.

A. Proteins and Peptides

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

| Modified and Unusual Amino Acids | |
|---|---|
| Abbr. | Amino Acid |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |

TABLE 1-continued

Modified and Unusual Amino Acids

| Abbr. | Amino Acid |
|---|---|
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

B. Nucleic Acids and Vectors

In certain aspects of the invention, nucleic acid sequences encoding a fusion protein as a stabilized multimeric arginase may be disclosed. Depending on which expression system to be used, nucleic acid sequences can be selected based on conventional methods. For example, human arginase I and II contain multiple codons that are rarely utilized in *E. coli* that may interfere with expression, therefore the respective genes or variants thereof may be codon optimized for *E. coli* expression. Various vectors may be also used to express the protein of interest, such as a fusion multimeric arginase or a cysteine-substituted arginase. Exemplary vectors include, but are not limited, plasmid vectors, viral vectors, transposon or liposome-based vectors.

C. Host cells

Host cells, preferably eukaryotic cells, useful in the present invention are any that may be transformed to allow the expression and secretion of arginase and fusion multimers thereof. The host cells may be bacteria, mammalian cells, yeast, or filamentous fungi. Various bacteria include *Escherichia* and *Bacillus*. Yeasts belonging to the genera *Saccharomyces, Kluyveromyces, Hansenula,* or *Pichia* would find use as an appropriate host cell. Various species of filamentous fungi may be used as expression hosts including the following genera: *Aspergillus, Trichoderma, Neurospora, Penicillium, Cephalosporium, Achlya, Podospora, Endothia, Mucor, Cochliobolus* and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) and *Schizosaccharomyces pombe*; filamentous fungi, e.g., *Aspergillus nidulans, Aspergillus awamori* (Ward, 1989), *Trichoderma reesei* (Penttila et al., 1987; Harkki et al, 1989).

Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCCCRL 1548) SV40-transformed monkey kidney cells (COS-1; ATCC CRL 1650) and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the arginase and/or their fusion multimers are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of the proteins are achieved.

D. Protein Purification

Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide always be provided in their most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, a stabilized arginase multimeric fusion protein, or an arginase prior or post pegylation. For example, a His tag or an affinity epitope may be comprised in such a arginase variant to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes such as proteins and industrial polymers. Typically, when an aqueous solution is used to transport the sample through the column, the technique is known as gel filtration chromatography, versus the name gel permeation chromatography which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or High pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

V. Pharmaceutical Compositions

It is contemplated that the novel arginases of the present invention can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g. cancer that the surgery failed to eliminate) does not survive.

It is not intended that the present invention be limited by the particular nature of the therapeutic preparation. For example, such compositions can be provided in formulations together with physiologically tolerable liquid, gel or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Where clinical applications are contemplated, it may be necessary to prepare pharmaceutical compositions—expression vectors, virus stocks, proteins, antibodies and drugs—in a form appropriate for the intended application. Generally, pharmaceutical compositions of the present invention comprise an effective amount of one or more arginase variants or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one arginase variant, such as a stabilized multimeric arginase or a pegylated arginase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

The present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed., 1990, incorporated herein by reference).

The arginase variants may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semisolid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include arginase variants, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the stabilized multimeric arginase or pegylated arginase may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

VII. Definitions

The term "aa" refers to amino acid(s). Amino acid substitutions are indicated by the amino acid position, e.g. 303, in the molecule using a letter code (the letter in front of the number indicates the amino acid being replaced, while the letter after the number indicates the amino acid being introduced).

As used herein the term "portion" when in reference to a protein (as in "a portion of a given protein") refers to fragments of that protein. The fragments may range in size from four amino acid residues to the entire amino acid sequence minus one amino acid.

As used herein the terms "protein" and "polypeptide" refer to compounds comprising amino acids joined via peptide bonds and are used interchangeably.

As used herein, the term "fusion protein" refers to a chimeric protein containing the protein of interest (i.e., a human arginase or variant thereof) joined (or operably linked) to an exogenous protein fragment (the fusion partner which consists of a non-arginase protein). The fusion partner may enhance serum half-life, solubility, or both. It may also provide an affinity tag (e.g. his-tag) to allow purification of the recombinant fusion protein from the host cell or culture supernatant, or both.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "$K_m$" as used herein refers to the Michaelis-Menton constant for an enzyme and is defined as the concentration of the specific substrate at which a given enzyme yields one-half its maximum velocity in an enzyme catalyzed reaction.

The term $k_{cat}$ as used herein refers to the turnover number or the number of substrate molecule each enzyme site converts to product per unit time, and in which the enzyme is working at maximum efficiency.

The term Kcat/Km as used herein is the specificity constant which is a measure of how efficiently an enzyme converts a substrate into product.

The term "Mn-hArgI" refers to human Arginase I with an Mn (II) cofactor. The term "Co-hArgI" refers to human Arginase I (mutant or native) with a Co (II) cofactor.

The term "$IC_{50}$" is the half maximal (50%) inhibitory concentration (IC) and thus a measure of effectiveness.

The term "pegylated" refers to conjugation with polyethylene glycol (PEG), which has been widely used as a drug carrier, given its high degree of biocompatibility and ease of modification. (Harris et al., 2001). Attachment to various drugs, proteins, and liposomes has been shown to improve residence time and decrease toxicity. (Greenwald et al., 2000; Zalipsky et al., 1997). PEG can be coupled (e.g. covalently linked) to active agents through the hydroxyl groups at the ends of the chain and via other chemical methods; however, PEG itself is limited to at most two active agents per molecule. In a different approach, copolymers of PEG and amino acids have been explored as novel biomaterials which would retain the biocompatibility properties of PEG, but which would have the added advantage of numerous attachment points per molecule (providing greater drug loading), and which can be synthetically designed to suit a variety of applications (Nathan et al., 1992; Nathan et al., 1993).

The term "gene" refers to a DNA sequence that comprises control and coding sequences necessary for the production of a polypeptide or precursor thereof. The polypeptide can be encoded by a full length coding sequence or by any portion of the coding sequence so long as the desired enzymatic activity is retained.

The term "subject" refers to animals, including humans.

The term "wild-type" refers to a gene or gene product which has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "variant" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

VIII. Kits

The present invention provides kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a stabilized multimeric arginase or isolated pegylated arginase, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

IX. EXAMPLES

The following examples serve to illustrate certain preferred embodiments and aspects of the present invention and are not to be construed as limiting the scope thereof. In the experimental disclosure which follows, the following abbreviations apply: eq (equivalents); M (Molar); µM (micromolar); mM (millimolar); N (Normal); mol (moles); mmol (millimoles); µmol (micromoles); nmol (nanomoles); g (grams); mg (milligrams); µg (micrograms); L (liters); ml (milliliters); µl (microliters); cm (centimeters); mm (millimeters); µm (micrometers); nm (nanometers); EC (degrees Centigrade); MW (molecular weight); PBS (phophate buffered saline); min (minutes).

Example 1

Gene Synthesis and Expression of Human Arginase I & II

The human Arginase I and II genes both contain mutiple codons that are rarely utilized in *E. coli* that can interfere with expression. Thus, in order to optimize protein expression in *E. coli*, the respective genes were assembled with codon optimized oligonucleotides designed with DNA-Works software (Hoover et al., 2002). Each construct contains an N-terminal NcoI restriction site, an in-frame N-terminal His$_6$ tag followed by a Tobacco Etch Virus (TEV) protease site and a C-terminal BamHI site for simplifying cloning. Cleavage by TEV protease removes the His6 peptide and the N-terminal Met of arginase. An Arginase II gene was designed with a TEV protease cleavage site and without the first native 21 aa. The first 21 aa are a putative mitochondrial-targeting sequence and its removal results in greater protein yield and stability (Colleluori et al., 2001). After cloning into a pET28a vector (Novagen), *E. coli* (BL21) containing an appropriate Arginase expression vector were grown at 37° C. using Terrific Broth (TB) media containing 50 µg/ml kanamycin in shake flasks at 250 rpm until reaching an OD$_{600}$ of 0.5-0.6. At that point the cultures were transferred to 25° C., induced with 0.5 mM IPTG and allowed to express protein for an additional 12 hrs. Cell pellets were then collected by centrifugation and re-suspended in an IMAC buffer (10 mM NaPO$_4$/10 mM imidazole/300 mM NaCl, pH 8). After lysis by a French pressure cell, lysates were centrifuged at 20,000×g for 20 min at 4° C., and the resulting supernatant was applied to a cobalt or nickel IMAC column, washed with 10-20 column volumes of IMAC buffer, and then eluted with an IMAC elution buffer (50 mM NaPO$_4$/250 mM imidazole/300 mM NaCl, pH 8). The desired divalent metal cation is incorporated by incubation with 10 mM metal (CoCl$_2$ or MnSO$_4$) for 15 min at 50°-55° C., followed by filtration through a 0.45 µm syringe filter. Using a 10,000 MWCO centrifugal filter device (Amicon), proteins were then buffer-exchanged several times into a 100 mM Hepes, 10% glycerol, pH 7.4 solution. Aliquots of Arginase enzyme were then flash frozen in liquid nitrogen and stored at −80° C. Arginase purified in this manner is >95% homogeneous as assessed by SDS-PAGE and coomassie staining (FIG. 2). The yield is calculated to be ~200 mg/L culture based upon the calculated extinction coefficient, $\epsilon_{280}$=24,180 M$^{-1}$ cm$^{-1}$ in a final buffer concentration of 6 M guanidinium hydrochloride, 20 mM phosphate buffer, pH 6.5 (Gill and von Hippel, 1989).

Example 2

Incorporating and Determining Metal Content in Arginase I

As mentioned in Example 1, incorporation of Mn$^{2+}$ and Co$^{2+}$ can be achieved by purifying Arginase, followed by an incubation step with 10 mM metal at 50° C. for 10 min. In order to determine the final metal content and identity of the Arginase preps, protein samples of Mn-hArgI (145 µM), Co-hArgI (182 µM) and associated dialysis buffers (100 mM Hepes, pH 7.4) were diluted in 2% nitric acid and analyzed by inductively coupled plasma mass spectrometry (ICP-MS, Department of Geological Sciences, University of Texas at Austin) to quantify the protein's cobalt, iron, manganese and zinc content by subtracting the concentration of metals found in dialysis buffer from the metal concentration of the final protein samples and dividing by protein concentration. To determine protein concentrations, an extinction coefficient was calculated for hArgI based on amino acid sequence (Gill and von Hippel, 1989). All protein concentrations for Arginase I were calculated based upon the calculated $\epsilon_{280}$=24,180 M$^{-1}$ cm$^{-1}$ in a final buffer concentration of 6 M guanidinium hydrochloride, 20 mM phosphate buffer, pH 6.5. For comparison, Arginase concentration was also calculated by BCA assay using dilutions of BSA as a standard. Using this method it was found that Arginase samples incubated with Co$^{2+}$ contain 2.1±0.5 equivalents Co and 0.4±0.1 equivalents Fe, with no detectable amounts of Zn or Mn. Samples incubated with Mn$^{2+}$ contain 1.5±0.2 equivalents Mn and 0.4±0.1 equivalents Fe, and no detectable amounts of Zn or Co. Thus, heat incubation is an efficient method for incorporation of Cobalt.

Example 3

Incorporating and Determining Metal Content in Arginase II

Efficient metal incorporation into Arginase II was achieved by culturing *E. coli* harboring the ArgII gene in minimal media until an OD$_{600}$ of 1 is reached, whereupon the protein was expressed with 1 mM IPTG and 100 µM CoCl$_2$ for an additional 12 hrs. In order to determine the final metal content and identity of the Arginase preps, protein samples of Co-hArgI (290 µM) and associated dialysis buffers (100 mM Hepes, pH 7.4) were diluted in 1% nitric acid and analyzed by inductively coupled plasma mass spectrometry (ICP-MS, Department of Geological Sciences, University of Texas at Austin) to quantify the protein's cobalt, iron, manganese and zinc content by subtracting the concentration of metals found in dialysis buffer from the metal concentration of the final protein samples and dividing by protein concentration. To determine protein concentrations, an extinction coefficient was calculated for hArgI based on amino acid sequence (Gill and von Hippel, 1989). All protein concentrations for Arginase II were calculated based upon the calculated $\epsilon_{280}$=22,900 $M^{-1}$ $cm^{-1}$ in a final buffer concentration of 6 M guanidinium hydrochloride, 20 mM phosphate buffer, pH 6.5. For comparison, Arginase concentration was also calculated by BCA assay using dilutions of BSA as a standard. Using this method it was found that Arginase samples expressed with $Co^{2+}$ contain 1.35±0.1 equivalents Co and 0.63±0.1 equivalents Fe, with no detectable amounts of Zn or Mn.

Example 4

Steady State Kinetics of Cobalt Arginase I at Physiological pH

Figure 3:
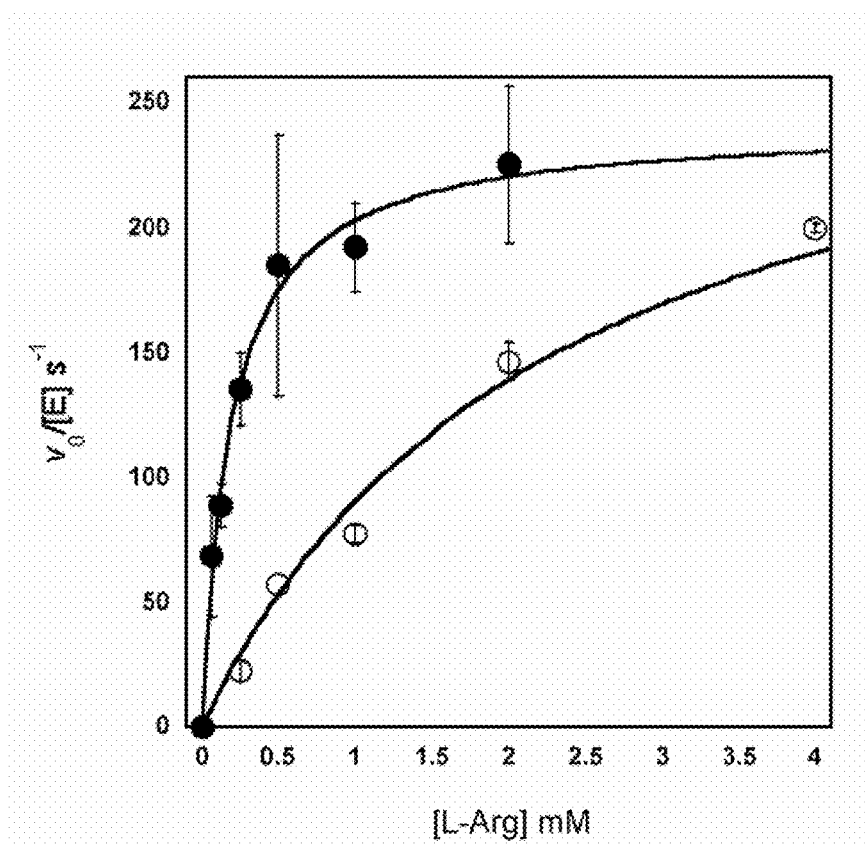
FIG. 3 is a representative graph of steady-state kinetics of L-arginine hydrolysis by Co-hArgI (•) and Mn-hArgI (○) in a 100 mM Hepes buffer, pH 7.4, 37° C. Co-hArgI had a $k_{cat}$ of $240\pm14$ s$^{-1}$, a $K_M$ of $190\pm40$ μM, and $k_{cat}/K_M$ of $1,270\pm330$ mM$^{-1}$ s$^{-1}$. Mn-ArgI had a $k_{cat}$ of $300\pm12$ s$^{-1}$, a $K_M$ of $2,330\pm260$ μM, and $k_{cat}/K_M$ of $129\pm20$ mM$^{-1}$ s$^{-1}$.

Diacetylmonoxine (DAMO) dervitization of urea products in the presence of strong acids, thiosemicarbazide and $Fe^{3+}$ with heating to produce a chromophore with a $\lambda_{max}$ of ~530 nm, was used to monitor urea production following hydrolysis of L-Arginine by arginase. The dye structure is not definitively known, but the reaction is hypothesized to be a condensation of DAMO and urea/uriedo that is possibly stabilized by $Fe^{3+}$ ions (Beale and Croft, 1961). A standard curve of urea vs. $A_{530}$ was constructed that was found to be linear between 0-300 µM urea with a lower detection limit of 1-2 µM. The steady-state kinetics of Co-hArgI, and Mn-hArgI were examined over a range of L-arginine concentrations (0-40 mM) in a 100 mM Hepes buffer pH 7.4, 37° C. Typically reactions were performed by equilibrating 200 µL in 1.5 ml eppendorf tubes at 37° C. in a heat block, starting the reaction by adding 5 µL of enzyme for 30 sec and quenching with 15 µL of 12 N HCl. Reactions and blanks were then mixed with 800 µL of color developing reagent (COLDER) (Knipp and Vasak, 2000) and boiled for 15 min. After cooling for 10 min, the samples were transferred to cuvettes and read at 530 nm on a spectrophotometer. L-Arginine has a background absorbance that makes correction necessary, so L-Arginine blanks were included for all concentrations used. The resulting data is then corrected for background and the concentrations of product formed calculated from the standard curve. The product is then divided by the time and the concentration of enzyme used and $v_o/[E]$ is plotted vs. substrate concentration and fit directly to the Michaelis-Menten equation (FIG. 3), where $v_o/[E]=k_{cat}*[S]/([S]+K_M)$. With this method, Co-hArgI had a $k_{cat}$ of 240±14 $s^{-1}$, a $K_M$ of 190±40 µM, and $k_{cat}/K_m$ of 1,270±330 $mM^{-1}$ $s^{-1}$," as compared to Mn-hArgI, which had a $k_{cat}$ of 300±12 $s^{-1}$, a $K_M$ of 2,330±260 µM, and $k_{cat}/K_M$ of 129±20 $mM^{-1}$ $s^{-1}$. The use of Cobalt as a cofactor at physiological pH leads to 10 fold increase in the specificity constant.

Example 5

Steady State Kinetics of Cobalt Arginase II at Physiological pH

Arginase II purified as described in Example 3 and characterized as described in Example 4 was found to have a $k_{cat}$ of 182±7 $s^{-1}$, a $K_M$ of 126±18 µM, and a $k_{cat}/K_M$ of 1,440±260 $mM^{-1}$ $s^{-1}$ as compared to Mn-hArgII where we found a $k_{cat}$ of 48±2 $s^{-1}$, a $K_M$ of 2,900±300 µM, and $k_{cat}/K_M$ of 17±2 $mM^{-1}$ $s^{-1}$. The use of Cobalt as a cofactor at physiological pH leads to 80 fold increase in the specificity constant for Arginase II.

Example 6

96-Well Plate Screen for Arginase Activity and Ranking Clones

Arginase hydrolysis of L-Arginine produces L-Ornithine and urea. The L-Arginine hydrolysis assay of Example 3 was adapted to 96-well plate format for the detection of urea and used for screening libraries of protein mutants and for rank-ordering clones with the greatest Arginase activity. Clones displaying greater than 2-fold increase in activity were selected for further characterization. The assay was shown to have a dynamic range of ~5-200 µM for ureido product detection. More than 500 clones can easily be screened per day via manual screening. The signal output, i.e., color intensity, reflects three main parameters, namely the specificity constant ($k_{cat}/K_M$), the enzyme concentration [Enz], and time (t). If necessary, enzyme levels in individual clones can be detected by ELISA; however, generally enzyme expression of Arginase varies less than two-fold and therefore expression differences do not constitute a significant issue.

Single colonies were picked into 96-well culture plates containing 75 µL of TB media/well containing 50 µg/ml kanamycin. These cultures were then grown at 37° C. on a plate shaker until reaching an $OD_{600}$ of 0.8-1, cooled to 25° C., whereupon an additional 75 µL of media containing 50 µg/ml kanamycin, and 0.5 mM IPTG was added. Expression was performed at 25° C. with shaking for ~2 hrs, following which 100 µL of culture/well was transferred to a 96 well assay plate. The assay plates were then centrifuged to pellet the cells, the media was removed, and the cells were lysed by addition of 50 µL/well of B-PER protein extraction reagent (Pierce). An additional 50 µL/well of 200 µM L-Arginine, 1 mM $CoCl_2$, in a 100 mM HEPES buffer, pH 7.4 was subsequently added and allowed to react at 37° C. After reacting ~1-2 min, 100 µL/well of color developing reagent are added and the plate was processed (Knipp and Vasak, 2000). Colonies having the ability to produce urea resulted in formation of a bright red dye with a $\lambda_{max}$ of 530 nm.

Example 7 pH Rate Dependence of Cobalt Arginase and Manganese Arginase

To examine the pH dependence of $k_{cat}/K_M$ of cobalt and manganese substituted Arginase, the steady-state kinetic constants were determined across a broad range of pH values. The following buffers were used: sodium acetate (pH 5-5.5), MES (pH 6-6.5), HEPES (pH 7-7.8), Tris (pH 8-9), Capso (pH 9-10.5), all at a 100 mM concentration. All kinetics were determined in at least triplicate at 37° C. After fitting the kinetic data to the Michaelis-Menten equation, the $k_{cat}/K_M$ values were calculated and fit to a Henderson-Hasselbach equation to determine $pK_a$ values. Because fits to two $pK_a$ values closer than 3.5 units tend to underestimate $\gamma_{max}$, Segel's method was used to calculate corrected $pK_a$ values for each limb of the $k_{cat}/K_M$ profiles (Segel, 1975). Adjusted fits of $k_{cat}/K_M$ vs. pH resulted in a bell shaped curve with Co-hArgI having an ascending limb $pK_a$ of 7.5±0.1 and a descending limb $pK_a$ of 9.8±0.1. Mn-hArgI also had a bell shaped curve with an ascending limb $pK_a$ of 8.5±0.1 and a descending limb displaying an apparent $pK_a$ value of 10.1±0.1 (FIG. 4). Mn-hArgI and Co-ArgI enzymes exhibited a $\Delta pK_a$ of 1 pH units. This shift in $pK_a$ upon Co substitution likely imparts much of the observed improvement in the specificity constant. At physiological pH, approximately 44% of Co-hArgI would have hydroxide bound as opposed to 7% with Mn-hArgI.

Example 8

The Effect of Mutations at Position 303

An NNS codon saturation library at position 303 was constructed and screened using the following mutagenic primers:

Forward '5-cgatcacgttagcaNNSttcggtttagcccg (SEQ ID NO:3), and reverse '5-CGGGCTAAACCGAAsnnT-GCTAACGTGATCG (SEQ ID NO:4), using the hArgI gene as template DNA and specific end primers; forward '5-GATATACCATGGGTTCTTCTCACCAT-CATCACCACCACAGCTCTGGCG (SEQ ID NO:5) and; reverse '5-CGAATTCGGATCCTCACTTCGGTGGAT-TCAGATAATCAATT (SEQ ID NO:6). The PCR product digested with NcoI and BamHI and ligated into pET28a vector with T4 DNA ligase. The resulting ligation was transformed directly into *E. coli* (BL21), plated on LB-kanamycin plates for subsequent screening as described in Example 4. Clones exhibiting highest activity were isolated and the DNA was sequenced. The respective enzyme variants were purified as described in Example 1 and heat incubated with Cobalt as described in Example 2. All proteins were purified to >95% homogeneity as assessed by SDS-PAGE. Arginine hydrolysis kinetics were determined with a range of L-arginine concentrations (0-2 mM) at 37° C. in a 100 mM Hepes buffer pH 7.4, and the resulting data fit to the Michaelis-Menten equation in Kaleidagraph. $Cys_{303}$ substituted with Phe or Ile lead to a 2 fold & 1.6 fold increase in $k_{cat}/K_M$ respectively as compared to wild-type Co-hArgI. Leu, Pro, His, and Arg substitutions had about 90% of wild-type activity.

The $Cys_{303}$ variants were also tested for serum stability at 37° C. as follows: Purified enzymes were added to pooled human serum (Innovative) at a concentration of 1 μM and incubated at 37° C. Every ~24 hours, aliquots were withdrawn and tested in triplicate for their ability to hydrolyze 1 mM L-arginine in a 100 mM Hepes buffer pH 7.4. After ~4 days the resulting data was fit to either an exponential or logistic decay model to calculate $T_{1/2}$ values. The stability of the wild-type enzyme was used as a standard and was calculated to be a $T_{1/2}$ of 33±3 hrs. Enzymes substituted with Phe, Ile, Leu, and His were only about half as stable as wild-type. Mn-hArgI (○) displayed an exponential loss of activity with a T ½ life of 4.8±0.8 hrs. In contrast Co-hArgI (•) displayed a bi-phasic loss of activity with an apparent first T½ of 6.1±0.6 hrs followed by much longer second T ½ of 37±3 hrs.

Example 9

Substrate Specificity

Figure 6:
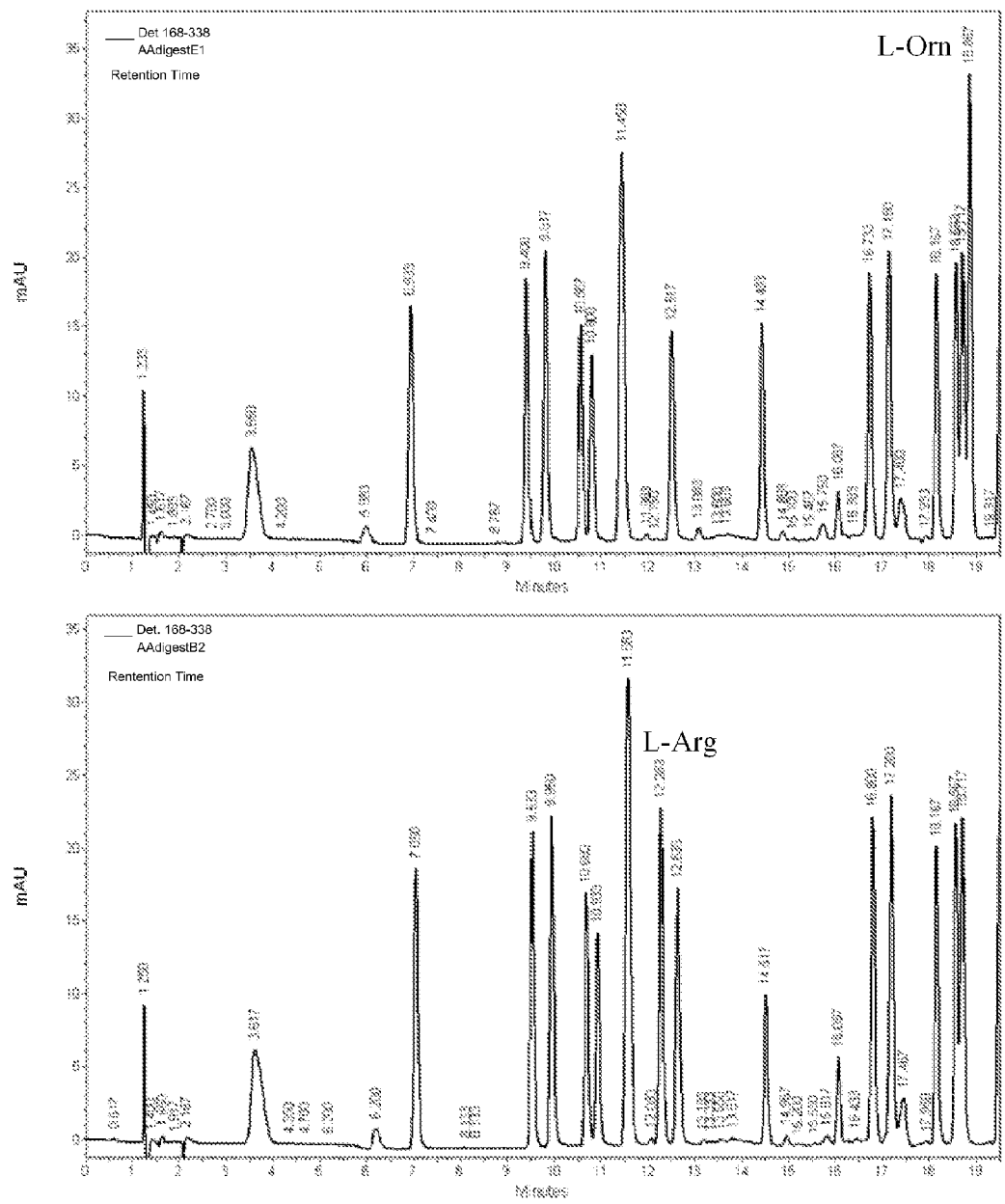
FIG. 6 is a graph showing HPLC traces of the 20 standard amino acids incubated with either Co-hArgI (Top panel) or dialysis buffer (Lower Panel). Co-hArgI incubated with the 20 standard amino acids resulted in the loss of a single peak at RT=12.3 min, matching that of L-Arginine controls, and the appearance of a single new peak at RT=18.8 min, matching that of L-Ornithine controls.

The selectivity of the engineered human Arginase for the hydrolysis of arginine was evaluated. Co-hArgI (1 μM) or dialysis buffer was incubated with all 20 aa (5 mM each) for 12 hr at 37° C. in a 220 mM phosphate buffer pH 7.4. Standards, controls and experiments were derivatized with OPA and FMOC (Agilent) and separated on a C18 reverse phase HPLC column (Agilent) (5 μm, 4.6×150 mm) essentially as described by Agilent Technologies (Publication Number: 5980-3088) except for modification of the separation protocol slightly by reducing the flow rate by ½ and doubling the acquisition time to get better peak separation. The 20 standard amino acids incubated with dialysis buffer showed 20 peaks with good resolution, and the 20 standard amino acids incubated with Co-hArgI showed 20 peaks (FIG. 6) with disappearance of the L-Arginine peak (RT=12.3 min) and appearance of one new peak with a retention time matching that of L-Ornithine (RT=18.8 min). None of the other amino acids were observed to be affected by Co-hArg I.

Example 10

High Throughput Purification and Kinetic Screening of Variants

A small-scale purification scheme was developed to rapidly purify dozens of proteins at once and carry out high throughput enzyme kinetics analysis. 50 ml cultures of hArg I were expressed in 125 ml shake flasks as described in Example 1. 5 ml of the resulting culture were collected by centrifugation. The cell pellets were then lysed with 400 μL of B-PER protein extraction reagent (Pierce). The soluble fraction was mixed with 500 μL IMAC lysis buffer and 100 μL of IMAC beads in a 1.5 ml Eppendorf tube, incubated for two minutes and centrifuged at 3000 rpm for 20 s in a table top centrifuge. The supernatant was discarded and the beads are washed with 2×1 ml IMAC lysis buffer by mixing/centrifugation and discarding the supernatant. hArg I was then eluted from the beads by addition of 300 μL of IMAC elution buffer and another centrifuge step. The resulting hArg I containing supernatant was subjected to buffer exchange twice with a 100 mM Hepes, pH 7.4 buffer using a 10,000 MWCO centrifugal concentration device (YM-10 Amicon). The protein was then quantified by $A_{280}$, heated in the presence of Cobalt as above, and the resulting Co-hArg I was assessed by SDS-PAGE as described in Example 1. This method allows purification of 12-16 proteins in ~2 hrs with a yield of 200-300 μg protein at 90-95% purity as assessed by SDS-PAGE.

The enzyme variants were then tested for their ability to hydrolyze L-Arginine by incubating 24 nM of enzyme with 200 μM of L-arginine in microtiter plate wells. Aliquots were collected at different time points and directly quenched into the acidic color-developing reagent (COLDER). After developing the dye and reading the absorption, the progress curve data was fit to an exponential equation to estimate an apparent $k_{cat}/K_M$ value.

Example 11

Engineering the $2^{ND}$ Shell Metal Ligands of Arginase for Optimal Activity

The catalytic power of a metallohydrolase stems in part from its remarkable ability to depress the normal $pK_a$ value of water (~16) to a much lower value and coordinate the highly reactive hydroxide ion for attack on substrate. Both the kind of metal and its local environment comprising of $1^{st}$ and $2^{nd}$ shell ligands influence the $pK_a$ of the nucleophilic water/hydroxide molecule (Christianson and Cox, 1999). Metal (A) of hArgI is coordinated to the imidazole of H101, which is in turn hydrogen bonded to the hydroxyl of S230. Metal (B) of hArgI is coordinated to the imidazole of H126, which has a $2^{nd}$ shell hydrogen bond with the carboxyl of D181. An NNS codon saturation library at position 181 and 230 was constructed using the following mutagenic primers: (D181) Forward '5-cattggcttacgtNNSgtcgacccagg (SEQ ID NO:7), reverse '5-CCTGGGTCGACSNNACGTAAGCCAATG (SEQ ID NO:8); (S230) forward '5-cgtccaatccatctgNNSttcgatgttgacg (SEQ ID NO:9), reverse '5-CGTCAACATC-GAASNNCAGATGGATTGGACG (SEQ ID NO:10), along with the hArgI gene and specific end primers via overlap extension PCR. After cloning, the library was transformed in *E. coli* (BL21) and screened as described in Example 4. Novel clones were identified by sequencing, re-transformed into *E. coli* (BL21) and purified and kinetically characterized as described in Example 8. Variants displaying apparent activity ≧ to wild-type were purified in larger scale and assayed for their steady-state kinetic parameters of $k_{cat}$ & $K_M$. The following variants were found to have greater $k_{cat}/K_M$ constants than Co-hArgI: hArg I D181S: 1420±200 $s^{-1}$ $mM^{-1}$, hArg I D181E/S230A: 1,450±200 $s^{-1}$ $mM^{-1}$, hArg I S230C: 2,290±200 $s^{-1}$ $mM^{-1}$, and hArg I S230G: 2,340±70 $s^{-1}$ $mM^{-1}$.

Example 12

Figure 7A:
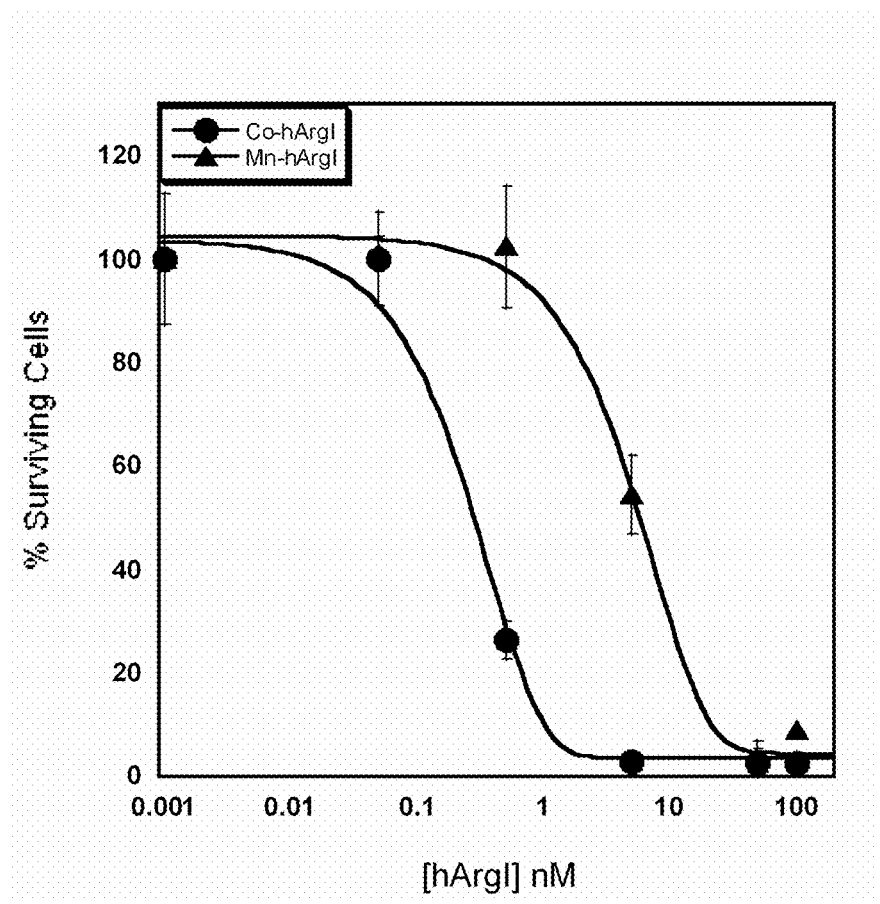
FIGS. 7A-B are graphs showing survival of HCC in tissue culture when treated with various arginase variants (along with controls).
Figure 7B:
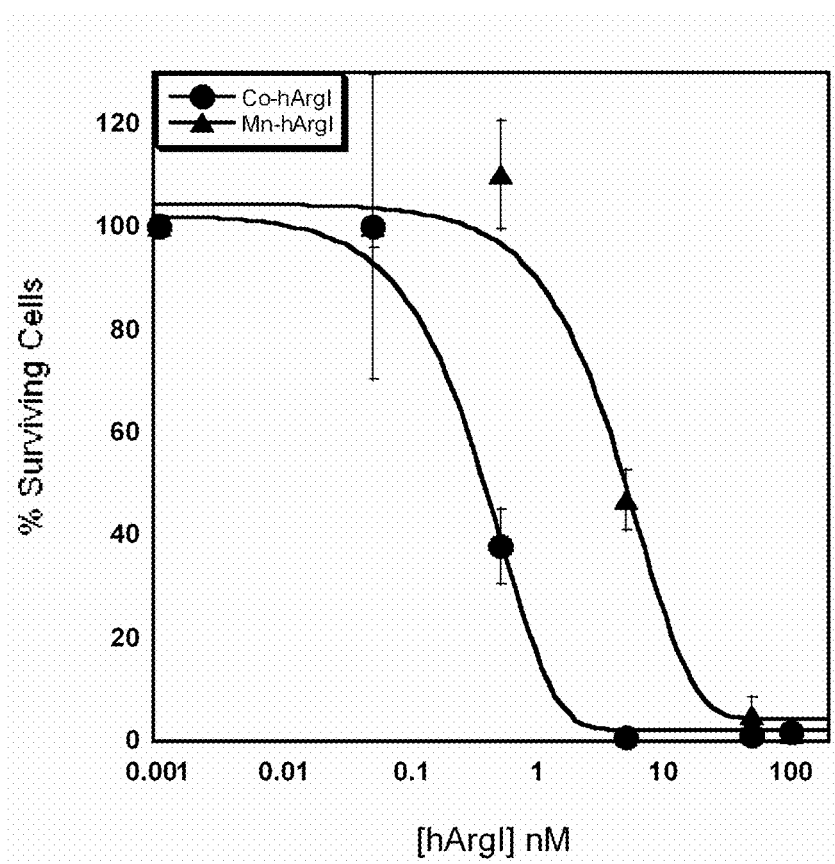

Cytotoxicty of Co-Arg and its Variants Towards Hepatocellular Carcinoma Cells and Metastatic Melanomas In order to test the in vitro cytoxicity of engineered Arginase, varying concentrations (0-100 nM) of Mn-ArgI, Co-ArgI, or Co-hArgI variants were incubated with HCC (Hep 3b) cells or melanoma (A375) cells (American Type Culture Collection) in 96-well plates at a seeding density of 500 cells/well, in DMEM media supplemented with fetal bovine serum. After 24 hours of incubation at 37° C., the cells were treated with Arginase containing media in triplicate at various concentrations. The control solution was a balanced salt solution in media. The treated cells were maintained at 37° C. and 5% $CO_2$. Cells were tested by standard MTT assay (Sigma-Aldrich) on days 1, 3, 5, & 7 by addition of 100 μL/well of MTT (5 mg/mL), and incubated for 4 hours with gentle agitation one to two times per hour. Following this, the solution was aspirated and 200 μL of DMSO was then added to each well. Absorbance at 570 nm was interpreted for each well using an automated plate reader to determine the relative number of surviving cells compared to controls. The resulting data was fit to an exponential equation to determine an apparent $IC_{50}$ value for Arginase cytotoxicity. FIG. 7A shows the effect of Mn-ArgI, or Co-ArgI addition on % MTT absorbance of HCC cells. The $IC_{50}$ values from day 5 were calculated, yielding an $IC_{50}$ value for Mn-hArgI of 5±0.3 nM (~0.18 μg/ml) and a value of 0.33±0.02 nM for Co-hArgI (~0.012 μg/ml). Thus, the Co-ArgI enzyme appears to be 15 fold more cytotoxic than the Mn substituted enzyme against HCC. Against the metastatic melanoma cell line (A375) Mn-hArgI (FIG. 7B) resulted in an apparent $IC_{50}$ of 4.1±0.1 nM (~0.15 μg/ml). Incubation with Co-hArgI lead to a 13-fold increase in cytotoxicity with an apparent $IC_{50}$ of 0.32±0.06 nM (~0.012 μg/ml).

Example 13

Engineering an Fc-Arginase Fusion Protein for Enhanced In Vivo Half-Life

Fusion to the IgG Fc domain has been employed extensively for prolonging the in vivo half-lives of therapeutic polypeptides such as the TNF-α inhibitor etanercept (Enbril®). The Fc domain binds to the FcγRn receptor, which is expressed on vascular endothelium and many other tissues (Roopenian and Akilesh, 2007). The affinity of FcγRn for the IgG Fc domain is strongly pH dependent. Binding occurs at the acidic pH of endosomal compartments allowing the protein to be recycled onto the cell surface and thus escape proteolytic degradation. At the cell surface, the Fc domain is released from FcγRn because the binding affinity is very low at physiological pH. Endosomal recycling via FcγRn is estimated to increase the serum half-life of immunoglobulins at least 4-7 fold, to about 7-14 days in humans. Fc fusions exploit this property to endow short lived molecules with a long half life. However, the human Arginase is a homotrimer and therefore if fused to the IgG Fc, which itself is a dimer, the resulting Fc-Arginase polypeptide will likely form high molecular weight aggregates.

Figure 8:
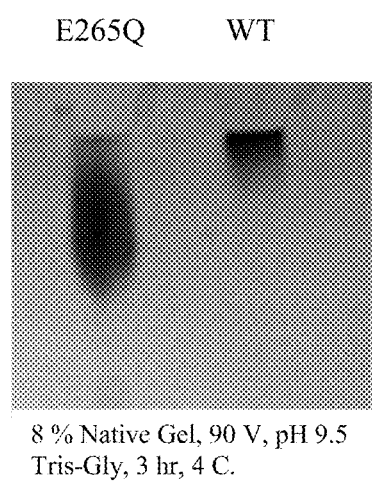
FIG. 8 is a photograph of a non-denaturing electrophoretic gel showing that the hArgI-E256Q variant is monomeric as opposed to trimeric wild-type h-ArgI.
Figure 9:
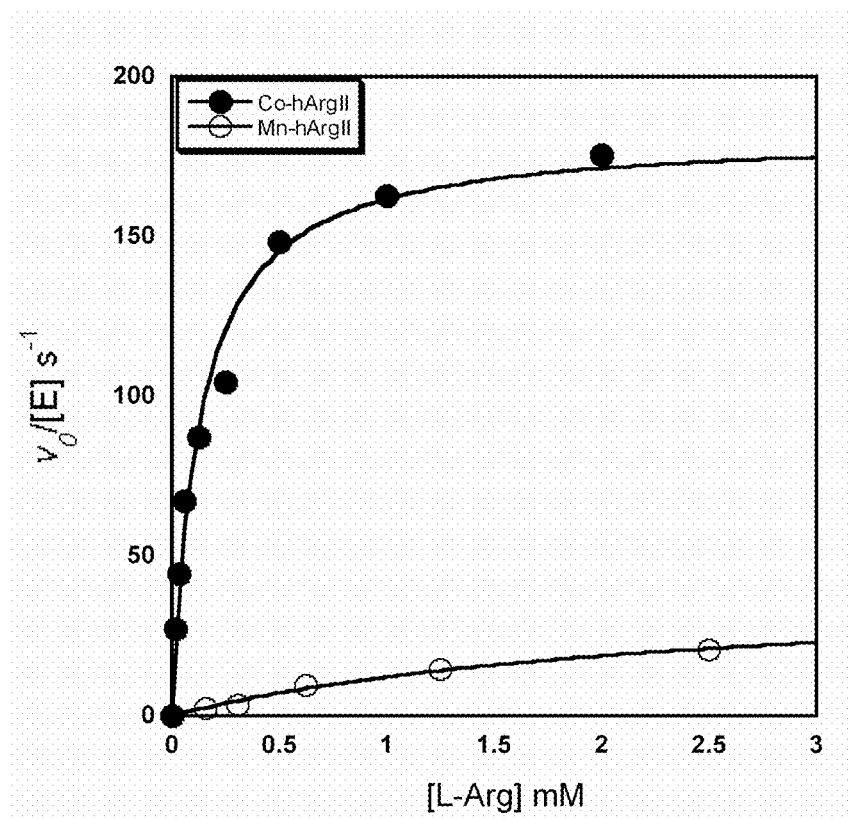
FIG. 9 is a representative graph of steady-state kinetics of L-arginine hydrolysis by Co-hArg-II (•) and Mn-hArg-II (○). Cobalt substituted hArg-II (•) hydrolysis of L-Arg at pH 7.4 and 37° C., with a $k_{cat}$ of 182±7 s$^{-1}$, a $K_M$ of 126±18 μM, and a $k_{cat}/K_M$ of 1,440±260 mM$^{-1}$ s$^{-1}$. Manganese substituted hArg-II (○) hydrolysis of L-Arg at pH 7.4 and 37° C., with a $k_{cat}$ of 48±2 s$^{-1}$, a $K_M$ of 2,900±300 μM, and $k_{cat}/K_M$ of 17±2 mM$^{-1}$ s$^{-1}$.

This problem was avoided by employing mutant forms of Arginase that disrupt trimerization and are stable in the monomeric form. The trimerization and subunit interface of Arginase I have been studied in some detail (Lavulo et al., 2001). A single aa substitution at Glu256Gln has been shown to disrupt trimerization resulting in the formation of monomeric Arginase I enzyme (Sabio et al., 2001). This mutation was introduced into hArgI by the use of two mutagenic primers: Forward '5-ggtttaacgtatcgcCAGggcctgtatatcacgg (SEQ ID NO:11) and Reverse '5-CCGTGATATACAGGCCCTGGC-GATACGTTAAACC (SEQ ID NO:12), and two specific end primers (Example 1) through overlap extension PCR, and cloning into a pET28a vector. After expression and purification of this variant, the steady-state kinetic analysis revealed nearly identical activity compared to Co-hArgI with a $k_{cat}/K_M$ of 1,320 $s^{-1}$ $mM^{-1}$. FIG. 8 shows a non-denaturing PAGE gel showing that Co-hArgI-E256Q is a monomer, as expected.

This construct was then cloned into Fc expression vectors available. The Fc expression vector is a construct based on a pTRC99a plasmid (Amersham) that contains a DsbA leader sequence followed by the IgG Fc coding region, an EcoRI restriction site and a stop codon. The monomeric Arginase gene was placed in frame behind the Fc coding region by digesting both vector and gene with EcoRI, and was subsequently ligated and transformed into *E. coli* (BL21) for sequencing and expression. Since the IgG Fc is normally a glycosylated protein, expression of recombinant IgGs or of Fc fusions has so far been carried out in recombinant mammalian cells that, unlike bacteria, are capable of N-linked glycosylation. However, while glycosylation at Asn297 is critical for the binding to the activating and inhibitory Fcγ receptors (FcγRI-III in humans) it does not have a noticeable effect on the affinity or pH dependent binding to FcγRn (Tao and Morrison, 1989; Simmons et al., 2002). Thus, aglycosylated IgG antibodies expressed in bacteria exhibit serum persistence in primates nearly indistinguishable from that of fully glycosylated antibodies expressed in mammalian cells (Simmons et al., 2002). In contrast to prevailing earlier notions, IgG antibodies and Fc proteins can be expressed efficiently in *E. coli* up to g/L levels in fermenters. *E. coli* expression is technically much simpler and faster. In addition, since the resulting protein is aglycosylated, it does not display glycan heterogeneity, an important issue in the expression of therapeutic glycoproteins (Jefferis, 2007). The fusion protein is purified by Protein A chromatography and the yield of correctly folded, dimeric Fc-Arginase fusion relative to polypeptides that fail to dimerize is quantified by FPLC gel filtration chromatography. This formulation has lead to a highly active and very stable form of human Arginase, suitable for in vivo trials.

Example 14

Pegylation of Arginase

Arginase was purified as described in Example 10 with one exception: after binding to the IMAC column, the protein was washed with extensively (80-90 column volumes) with an IMAC buffer containing 0.1% Triton 114 (This step removes most of the endotoxin), 10-20 column volumes of IMAC buffer, and then eluted with an IMAC elution buffer (50 mM $NaPO_4$/250 mM imidazole/300 mM NaCl, pH 8). Arginase was buffer exchanged into a 100 mM $NaPO_4$ buffer at pH 8.3 using a 10,000 MWCO filtration device (Amicon). Using a small reaction jar, Methoxy PEG Succinimidyl Carboxymethyl Ester 5000 MW (JenKem Technology) was added to Arginase at 40:1 molar ratio and allowed to react for 1 hr at 25° C. under constant stirring. The resulting mixture was then made 10 mM with $CoCl_2$ and heated at 50° C. for 10 minutes. After centrifuging to remove any precipitates, the PEG-5000 Arginase was extensively buffer exchanged (PBS with 10% glycerol) using a 100,000 MWCO filtration device (Amicon), and sterilized with a 0.2 micron syringe filter (VWR). All pegylated enzyme was analyzed for lipopolysaccharide (LPS) content using a *Limulus Amebocyte* Lysate (LAL) kit (Cape Cod Incorporated).

Figure 12:
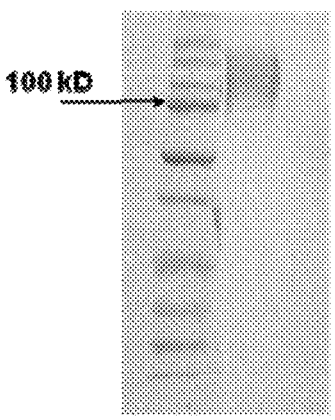

Pegylated Co-hArgI was found to have nearly identical serum stability to wt enzyme and displayed a $k_{cat}/K_M$ value of $1690\pm290$ $s^{-1}$ $mM^{-1}$. FIG. 12 shows a denaturing gel of the final product with an apparent MW of ~150 kDa.

Example 15

Serum Depletion of L-Arg in the Mouse Model

Figure 10:
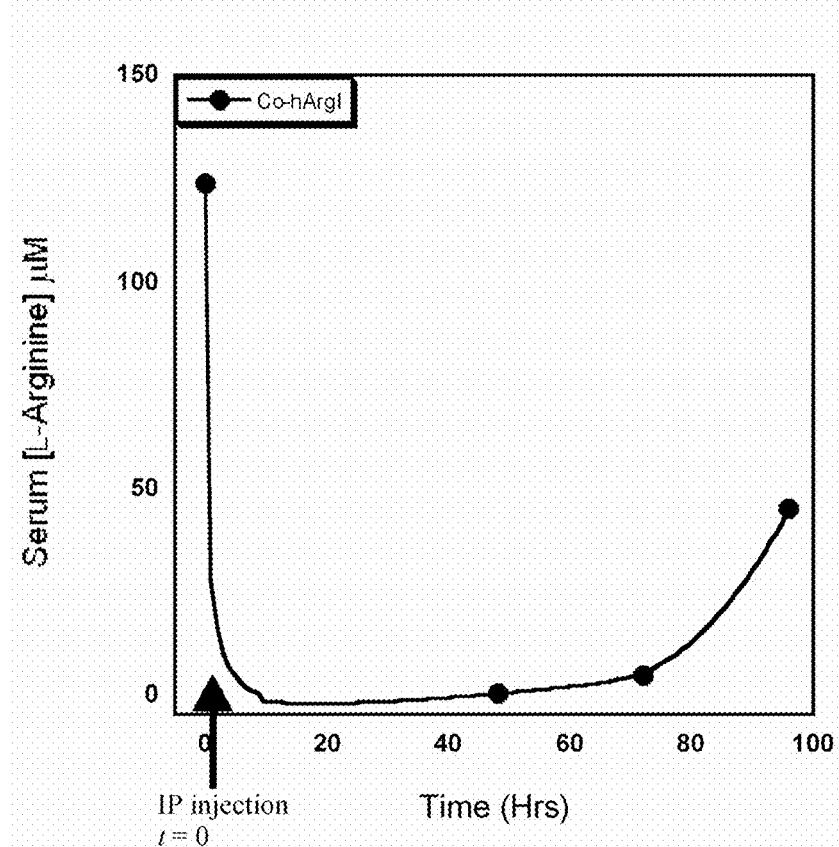
FIG. 10 is a graph showing serum L-arginine depletion in the mouse model. Serum L-Arg concentrations of Balb/c mice treated with a single IP dose of Co-hArgI are kept ≦ to 3-4 μM for over 3 days.

Balb/c mice were treated by single IP injection with 500 µg of pharmacologically prepared, pegylated Co-hArgI or an equal volume of PBS. Mice were sacrificed by cardiac venipuncture for blood collection at the time points of 0, 48, 72, and 96 hrs. Blood samples were immediately mixed 50:50 (v/v) with a 400 mM sodium citrate buffer pH 4 allowed to clot for 30 min and centrifuged for serum separation. The resulting serum was then filtered on 10,000 MWCO device (Amicon) for the removal of large proteins and precipitates and the flow-through was collected for analysis. L-arginine standards, control mouse serum and experiments were derivatized with OPA (Agilent) and separated on a C18 reverse phase HPLC column (Agilent) (5 µm, 4.6×150 mm) essentially as described by Agilent Technologies (Publication Number: 5980-3088) except for modification of the separation protocol slightly by reducing the flow rate by ½ and doubling the acquisition time to get better peak separation. An L-arginine standard curve was constructed by plotting L-Arg peak area versus concentration in order to quantify serum L-Arg levels. A single dose of pharmacologically prepared Co-hArgI was sufficient to keep L-Arg at or below detection limits for over 3 days (FIG. 10).

Example 16

HCC Tumor Xenograft Treatment with Co-hArgI

Figure 11:
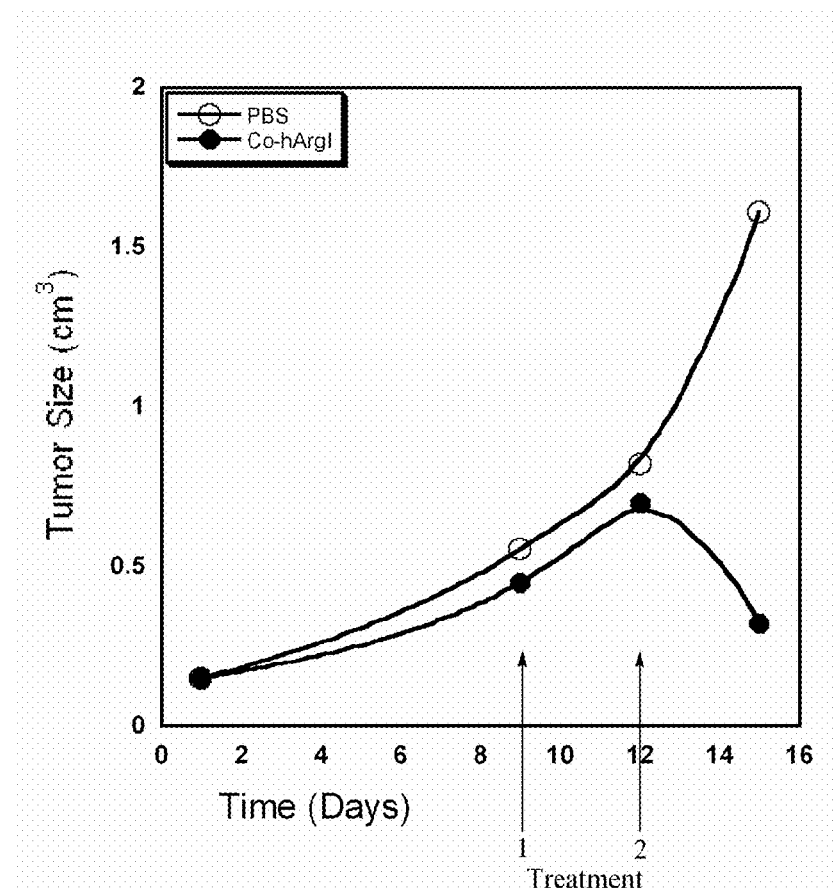
FIG. 11 is a graph showing HCC tumor xenograft reduction when treated with Co-hArgI as compared to controls. Nude mice bearing a Hep3b tumor xenografts were treated twice by IP injection with either PBS (○) or Co-hArgI (•) at day 9 and at day 12. Tumor shrinkage was observed in the mice treated with Co-hArgI whereas PBS treated tumors grew unchecked.

Nude mice were injected subcutaneously in the flank with ~$10^6$ HCC cells collected from a 75% confluent tissue culture. After the HCC xenografted tumors had grown to ~0.5 $cm^3$ in diameter (Day 9), mice were sorted into two groups. The experimental group received a 500 µg IP injection of pharmacologically optimized Co-hArgI at day 9 and at day 12. The control group received IP injections of PBS at days 9 and 12. As can be seen in FIG. 11, the PBS treated tumors had increased 3-fold in size by day 15. In stark contrast, Co-hArgI treated tumors had decreased in size by day 15. Mn-hArgI treated tumors had only been shown to be retarded in growth rate (Cheng et al., 2007). Co-hArgI appears to be a highly effective chemotherapeutic agent against HCCs both in vitro and in vivo.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Beale and Croft, *J. Clin. Pathol.*, 14:418-424, 1961.
Cama et al., *Biochemistry*, 42:7748-7758, 2003.
Cheng et al., *Cancer Lett.*, 224:67-80, 2005.
Cheng et al., *Cancer Res.*, 67:309, 2007.
Cheng et al., *Cancer Res.*, 67:4869-4877, 2007.
Christianson and Cox, *Annu. Rev. Biochem.*, 68:33-57, 1999.
Colleluori et al., *Arch. Biochem. Biophys.*, 389:135-143, 2001.
Dillon et al., *Med. Sci. Monit.*, 8:BR248-253, 2002.
Dowling et al., *Cell Mol. Life. Sci.*, 65(13):2039-55, 2008.
Durante et al., *Clin. Exp. Pharmacol. Physiol.*, 34:906-911, 2007.
Ensor et al., *Cancer Res.*, 62:5443-5450, 2002.
Feun et al., *J. Neurooncol.*, 82:177-181, 2007.
Gill and von Hippel, *Anal. Biochem.*, 182:319-326, 1989.
Greenwald et al., *Crit. Rev Therap Drug Carrier Syst.*, 17:101-161, 2000.
Harkki et al., *BioTechnology*, 7:596-603, 1989.
Harris et al., *Clin. Pharmacokinet.*, 40(7):539-51, 2001.
Hoover et al., *J. Biol. Chem.*, 277:37647-37654, 2002.
Hopwood et al., In: *Genetic Manipulation of Streptomyces*, A Laboratory Manual, The John Innes Foundation, Norwich, Conn., 1985.
Izzo et al., *J. Clin. Oncol.*, 22:1815-1822, 2004.
Jefferis, *Expert Opin. Biol. Ther.*, 7:1401-1413, 2007.
Knipp and Vasak, *Anal. Biochem.*, 286:257-264, 2000.
Lavulo et al., *J. Biol. Chem.*, 276:14242-14248, 2001.
Lopez et al., *Febs J.*, 272:4540-4548, 2005.
Lordanescu, *J. Bacteriol*, 12:597 601, 1975.
Mellor et al., *Gene*, 24:1-14, 1983.
Mora et al., *Biochemica Biophysica Acta*, 1476:181, 2000.
Nathan et al., *Bioconj Chem.*, 4:54-62, 1993.
Nathan et al., *Macromolecules*, 25:4476-4484, 1992.
Penttila et al., *Gene*, 61:155-164, 1987.
Remington's Pharmaceutical Sciences, 18th Ed. Mack Printing Company, 1289-1329, 1990.
Roopenian and Akilesh, *Nat. Rev. Immunol.*, 7:715-725, 2007.
Sabio et al., *FEBS Lett.*, 501:161-165, 2001.
Santhanam et al., *Circ. Res.*, 101:692-702, 2007.
Savoca et al., *Cancer Biochem. Biophys.*, 7:261-268, 1984.
Scolnick et al., *Biochemistry*, 36:10558-10565, 1997.
Scott et al., *Br. J. Cancer*, 83:800-810, 2000.
Segel, In: *Enzyme Kinetics*, John Wiley and Sons, Inc., New York, 1975.
Shen et al., *Cancer Lett.*, 231:30-35, 2006.
Sibakov et al., *Eur. J. Biochem.*, 145:567 572, 1984.
Simmons et al., *J. Immunol. Methods*, 263:133-147, 2002.
Tao et al., *J. Immunol.*, 143:2595-2601, 1989.
Ward, Embo-Alko Workshop on Molecular Biology of Filamentous Fungi, Helsinki, 119-128, 1989.
Wheatley and Campbell, *Pathol. Oncol. Res.*, 8:18-25, 2002.
Yoon et al., *Int. J. Cancer*, 120:897-905, 2007.
Zalipsky et al., *Bioconjug Chem.*, 8:111-118, 1997.

What is claimed is:

1. A composition comprising an isolated human Arginase I and a non-native metal cofactor, wherein the non-native metal cofactor is cobalt and the protein displays a kcat/Km for the hydrolysis of arginine between 400 $mM^{-1} s^{-1}$ and 4,000 $mM^{-1} s^{-1}$ at pH 7.4, further wherein the human Arginase I has an amino acid sequence as encoded by SEQ ID NO: 1, the composition being at physiological pH.

2. The composition of claim 1, wherein the amino acid sequence lacks an N-terminal methionine.

3. The composition of claim 1, wherein the human Arginase I is covalently linked to polyethylene glycol.

4. A pharmaceutical formulation comprising the composition of claim 1 and a pharmaceutically acceptable excipient and at physiological pH.

5. The formulation of claim 4, wherein the human Arginase I is covalently linked to polyethylene glycol.

* * * * *

UNITED STATES PATENT AND TRADEMARK OFFICE
CERTIFICATE OF CORRECTION

PATENT NO. : 8,440,184 B2  Page 1 of 1
APPLICATION NO. : 12/610685
DATED : May 14, 2013
INVENTOR(S) : George Georgiou and Everett Stone It is certified that error appears in the above-identified patent and that said Letters Patent is hereby corrected as shown below:

In the Specifications

In column 1, lines 13-18, delete
"STATEMENT REGARDING FEDERALLY SPONSORED RESEARCH OR DEVELOPMENT
This invention was made with government support under R01 CA139059 awarded by the National Institutes of Health. The government has certain rights in the invention."

Signed and Sealed this
Fourth Day of February, 2014

Michelle K. Lee
*Deputy Director of the United States Patent and Trademark Office*

SEQUENCE LISTING

<160> NUMBER OF SEQ ID NOS: 12

<210> SEQ ID NO 1
<211> LENGTH: 1044
<212> TYPE: DNA
<213> ORGANISM: Artificial Sequence
<220> FEATURE:
<223> OTHER INFORMATION: Synthetic primer

<400> SEQUENCE: 1

| | | | | | |
|---|---|---|---|---|---|
| gatataccat | gggttcttct | caccatcatc | accaccacag | ctctggcgag | aacctgtact | 60 |
| tccagtctgc | gaagagccgt | acgatcggca | ttattggtgc | gccgttctct | aaaggtcagc | 120 |
| cacgcggtgg | tgtggaagag | ggtccgacgg | ttctgcgtaa | ggccggttta | ttagaaaagc | 180 |
| tgaaagagca | ggagtgcgac | gttaaggact | acggtgactt | accattcgcg | gacatcccga | 240 |
| atgatagccc | gttccaaatc | gttaagaatc | gcgctctgt | gggtaaagca | agcgagcagt | 300 |
| tagcaggtaa | ggtggccgag | gtcaagaaaa | acggtcgtat | tagcctggtt | ttaggcggtg | 360 |
| atcatagctt | agcaattggc | tctatctctg | gtcatgcccg | tgtgcaccca | gatttaggtg | 420 |
| tcatttgggt | tgacgcccat | acggatatca | atacgccatt | aacgaccacc | agcggcaatc | 480 |
| tgcatggcca | gccggttagc | ttcttactga | aggagctgaa | gggtaaaatt | ccagatgttc | 540 |
| cgggctttag | ctgggtcacg | ccatgtatt | ctgccaagga | tatcgtgtac | attggcttac | 600 |
| gtgacgtcga | cccaggtgag | cactacatct | taaagaccct | gggtatcaag | tatttcagca | 660 |
| tgacggaagt | ggaccgctta | ggcatcggca | aggtgatgga | ggagacgctg | agctatctgc | 720 |
| tgggccgtaa | gaaacgtcca | atccatctga | gcttcgatgt | tgacggctta | gacccgagct | 780 |
| ttacgccagc | caccggcacg | ccggtcgttg | gtggtttaac | gtatcgcgaa | ggcctgtata | 840 |
| tcacggagga | aatctataag | acgggtttac | tgagcggtct | ggacattatg | gaggttaatc | 900 |
| caagcttagg | taagacgccg | gaagaagtta | cccgtaccgt | taacacggcg | gtcgcgatca | 960 |
| cgttagcatg | tttcggttta | gcccgcgagg | gcaaccataa | accaattgat | tatctgaatc | 1020 |
| caccgaagtg | aggatccgaa | ttcg | | | | 1044 |

<210> SEQ ID NO 2
<211> LENGTH: 1080
<212> TYPE: DNA
<213> ORGANISM: Artificial Sequence
<220> FEATURE:
<223> OTHER INFORMATION: Synthetic primer

<400> SEQUENCE: 2

| | | | | | |
|---|---|---|---|---|---|
| gatataccat | gggcagcagc | catcatcacc | accatcacag | ctctggtgaa | aacttatact | 60 |
| tccaaagcgt | ccatagcgtc | gcagtgattg | gtgccccgtt | tagccaaggt | caaaaacgca | 120 |
| agggtgttga | acatggtccg | gcagcgatcc | gcgaagcagg | tttaatgaag | cgtttaagca | 180 |
| gcttaggctg | tcacttaaag | gatttcggtg | atttaagctt | tacgccggtc | ccaaaggatg | 240 |
| atttatacaa | taatctgatc | gttaacccac | gctctgtggg | tctggcgaac | caggagctgg | 300 |
| cggaggtcgt | gtctcgtgca | gtcagcgacg | ttatagctg | cgttacgctg | ggcggtgatc | 360 |
| atagcttagc | cattggtacg | atttctggtc | atgcccgcca | ttgcccggat | ctgtgtgttg | 420 |
| tgtgggttga | tgcgcacgcg | gatatcaata | cgccactgac | cacgtctagc | ggtaatttac | 480 |
| acggccagcc | ggttagcttc | ttattacgtg | agctgcaaga | caaggtcccg | cagttaccag | 540 |
| gcttctcttg | gatcaaacca | tgtatcagca | gcgcatctat | tgtctacatt | ggcctgcgtg | 600 |

```
atgtcgaccc accggagcac ttcatcctga agaattatga catccagtat ttcagcatgc    660
gtgacatcga ccgtctgggt atccaaaaag ttatggagcg cacgttcgat ctgttaatcg    720
gcaagcgcca gcgtccgatt cacctgagct ttgacattga cgcctttgac ccgaccctgg    780
ccccagcaac gggcacgcca gtggttggtg gtttaaccta ccgtgagggt atgtatattg    840
cagaagagat ccataatacc ggcctgttat ctgccctgga tctggttgaa gtcaatccgc    900
agctggcaac ctctgaggag gaagcgaaga cgaccgccaa cctggcggtg gacgtcatcg    960
cctcttcttt cggccagacg cgtgaaggtg gccatatcgt gtatgaccaa ttaccaacgc   1020
catctagccc ggacgaatct gagaaccaag cacgtgtccg tatttgagga tccgaattcg   1080
```

<210> SEQ ID NO 3
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(16)
<223> OTHER INFORMATION: n is a, c, g, or t

<400> SEQUENCE: 3
cgatcacgtt agcannsttc ggtttagccc g                                    31

<210> SEQ ID NO 4
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(17)
<223> OTHER INFORMATION: n is a, c, g, or t

<400> SEQUENCE: 4
cgggctaaac cgaasnntgc taacgtgatc g                                    31

<210> SEQ ID NO 5
<211> LENGTH: 48
<212> TYPE: DNA
<213> ORGANISM: Artificial Sequence
<220> FEATURE:
<223> OTHER INFORMATION: Synthetic primer

<400> SEQUENCE: 5
gatataccat gggttcttct caccatcatc accaccacag ctctggcg                  48

<210> SEQ ID NO 6
<211> LENGTH: 41
<212> TYPE: DNA
<213> ORGANISM: Artificial Sequence
<220> FEATURE:
<223> OTHER INFORMATION: Synthetic primer

<400> SEQUENCE: 6
cgaattcgga tcctcacttc ggtggattca gataatcaat t                         41

<210> SEQ ID NO 7
<211> LENGTH: 27
<212> TYPE: DNA
<213> ORGANISM: Artificial Sequence
<220> FEATURE:
<223> OTHER INFORMATION: Synthetic primer
<220> FEATURE:

```
<221> NAME/KEY: misc_feature
<222> LOCATION: (14)..(15)
<223> OTHER INFORMATION: n is a, c, g, or t

<400> SEQUENCE: 7
cattggctta cgtnnsgtcg acccagg                                          27

<210> SEQ ID NO 8
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (13)..(14)
<223> OTHER INFORMATION: n is a, c, g, or t

<400> SEQUENCE: 8
cctgggtcga csnnacgtaa gccaatg                                          27

<210> SEQ ID NO 9
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (16)..(17)
<223> OTHER INFORMATION: n is a, c, g, or t

<400> SEQUENCE: 9
cgtccaatcc atctgnnstt cgatgttgac g                                     31

<210> SEQ ID NO 10
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(16)
<223> OTHER INFORMATION: n is a, c, g, or t

<400> SEQUENCE: 10
cgtcaacatc gaasnncaga tggattggac g                                     31

<210> SEQ ID NO 11
<211> LENGTH: 34
<212> TYPE: DNA
<213> ORGANISM: Artificial Sequence
<220> FEATURE:
<223> OTHER INFORMATION: Synthetic primer

<400> SEQUENCE: 11
ggtttaacgt atcgccaggg cctgtatatc acgg                                  34

<210> SEQ ID NO 12
<211> LENGTH: 34
<212> TYPE: DNA
<213> ORGANISM: Artificial Sequence
<220> FEATURE:
<223> OTHER INFORMATION: Synthetic primer

<400> SEQUENCE: 12
ccgtgatata caggccctgg cgatacgtta aacc                                  34
```